US012186171B2

United States Patent
Ohtsubo et al.

(10) Patent No.: US 12,186,171 B2
(45) Date of Patent: Jan. 7, 2025

(54) ELASTIC SHEET, UNDERPANTS-TYPE ABSORBENT ARTICLE, AND METHOD FOR MANUFACTURING ELASTIC SHEET

(71) Applicant: UNICHARM CORPORATION, Ehime (JP)

(72) Inventors: Toshifumi Ohtsubo, Kagawa (JP); Hirotomo Mukai, Kagawa (JP); Takahito Nagai, Kagawa (JP); Chieri Akino, Kagawa (JP); Satoshi Mizuno, Kagawa (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 18/585,408

(22) Filed: Feb. 23, 2024

(65) Prior Publication Data

US 2024/0189159 A1    Jun. 13, 2024

Related U.S. Application Data

(63) Continuation of application No. PCT/JP2022/032874, filed on Aug. 31, 2022.

(30) Foreign Application Priority Data

Aug. 31, 2021 (JP) .................................. 2021-141415

(51) Int. Cl.
*A61F 13/15*    (2006.01)
*A61F 13/49*    (2006.01)

(52) U.S. Cl.
CPC .. *A61F 13/49009* (2013.01); *A61F 13/15747* (2013.01); *A61F 13/49* (2013.01);
(Continued)

(58) Field of Classification Search
CPC .......... A61F 13/49009; A61F 13/15747; A61F 13/49; A61F 13/49011; A61F 13/49015;
(Continued)

(56) References Cited

U.S. PATENT DOCUMENTS

2020/0155370 A1    5/2020  Ohtsubo
2020/0260800 A1*   8/2020  Li ......................... A61F 13/496

FOREIGN PATENT DOCUMENTS

BR    112020002159 A2    7/2020
JP    2001504899 A       4/2001
(Continued)

OTHER PUBLICATIONS

Supplementary European Search Report issue in corresponding European Patent Application No. 22864666.7, dated Aug. 1, 2024 (4 pages).
(Continued)

*Primary Examiner* — Jacqueline F Stephens
(74) *Attorney, Agent, or Firm* — Osha Bergman Watanabe & Burton LLP

(57) ABSTRACT

A stretchable sheet includes a first sheet, a second sheet joined to the first sheet by welded portions, and an elastic member that is disposed between the first sheet and the second sheet and stretches and contracts in a continuous direction in which the elastic member extends. The welded portions are disposed on both sides of the elastic member in an intersecting direction intersecting with the continuous direction. Welded portion pairs are disposed in which the elastic member is sandwiched and restrict a position of the elastic member in the intersecting direction with respect to the first sheet and the second sheet. The elastic member has a damaged portion where a part of a surface of the elastic member is damaged. The welded portion pairs include a first welded portion pair and a second welded portion pair.

16 Claims, 22 Drawing Sheets

(52) U.S. Cl.
CPC ..... *A61F 13/49015* (2013.01); *A61F 13/4902* (2013.01); *A61F 2013/4903* (2013.01); *A61F 2013/49052* (2013.01)

(58) Field of Classification Search
CPC ........ A61F 13/4902; A61F 2013/15243; A61F 2013/49022; A61F 2013/49023; A61F 2013/49025; A61F 2013/49031; A61F 2013/49033; A61F 2013/49061; A61F 2013/49036; A61F 2013/49042; A61F 2013/51377; A61F 2013/8497
See application file for complete search history.

(56) References Cited

FOREIGN PATENT DOCUMENTS

| | | | |
|---|---|---|---|
| JP | 2009148531 A | 7/2009 | |
| JP | 2019150716 A | 9/2019 | |
| JP | 2020089438 A | 6/2020 | |
| JP | 2020137970 A | 9/2020 | |

OTHER PUBLICATIONS

Decision to Grant a Patent issued in corresponding Japanese Patent Application No. 2023-512792, dated Mar. 28, 2023, with translation (5 pages).
International Search Report issued in corresponding International Application No. PCT/JP2022/032874, dated Nov. 15, 2022, with translation (8 pages).
Written Opinion issued in corresponding International Application No. PCT/JP2022/032874, dated Nov. 15, 2022 (5 pages).
Brazilian Office Action issued in corresponding Brazilian Patent Application No. BR112024000616-6, dated Aug. 7, 2024 (5 pages).

* cited by examiner

ELASTIC SHEET, UNDERPANTS-TYPE ABSORBENT ARTICLE, AND METHOD FOR MANUFACTURING ELASTIC SHEET

BACKGROUND

Field

The present invention relates to a stretchable sheet, an underpants-shaped absorbent article, and a method for manufacturing a stretchable sheet.

Description of the Related Art

Conventionally, in an underpants-shaped absorbent article such as a disposable diaper, there is a stretchable sheet that has stretchability and that is used as a sheet member constituting a waist member. As such a stretchable sheet, there is known a type of stretchable sheet that exhibits stretchability by attaching stretched elastic members (such as elastic strings) between two sheet members so as to be sandwiched. For example, Patent Document 1 discloses a technique related to the following stretchable sheet: in the stretchable sheet, wire-like elements 5 that can stretch and contract in the lengthwise direction are placed being in the stretched state between two sleeves 1 and 1, and a plurality of connecting portions that join sleeves 1 and 1 together are formed, and the wire-like elements 5 are fixed by clamping them by narrowed portions 8 that are formed between two the connecting portions 6a and 6b adjacent to the wire-like element 5 in the transverse direction.

Patent Literature

Patent Documents 1: Japanese Patent Publication No. 2001-504899

In the stretchable sheet of Patent Document 1, string-like elastic members are clamped between a pair of welded portion pair (connecting portions 6a and 6b) that are formed using welding means, etc., and this makes it possible to manufacture the stretchable sheet without using an adhesive, etc. in order to fix the elastic members. However, in such a stretchable sheet, there is a possibility that its stretchability deteriorates due to falling off of elastic members from between the welded portion pair (narrowed portion 8) when elastic members stretch and its diameter becomes narrower.

SUMMARY

One or more embodiments provide a stretchable sheet in which stretchability is less likely to deteriorate.

A stretchable sheet according to one or more embodiments includes: a first sheet; a second sheet that is joined to the first sheet by a plurality of welded portions; and an elastic member that is provided between the first sheet and the second sheet, the elastic member being capable of stretching and contracting in a continuous direction in which the elastic member continues, the plurality of the welded portion being located on both sides of the elastic member in the intersecting direction that intersects with the continuous direction, a plurality of welded portion pairs being provided in which the elastic member is sandwiched and that restricts a position of the elastic member in the intersecting direction with respect to the first sheet and the second sheet, the elastic member having a damaged portion where a part of a surface of the elastic member is damaged, the welded portion pair having a first welded portion pair and a second welded portion pair that is located adjacent to the first welded portion pair in the continuous direction, at least one of the damaged portion being provided between the first welded portion pair and the second welded portion pair in the continuous direction.

Features of one or more embodiments other than the above will become clear by reading the description of the present specification with reference to the accompanying drawings.

According to one or more embodiments, it is possible to provide a stretchable sheet in which stretchability is less likely to deteriorate.

DESCRIPTION OF THE EMBODIMENTS

Figure 1:
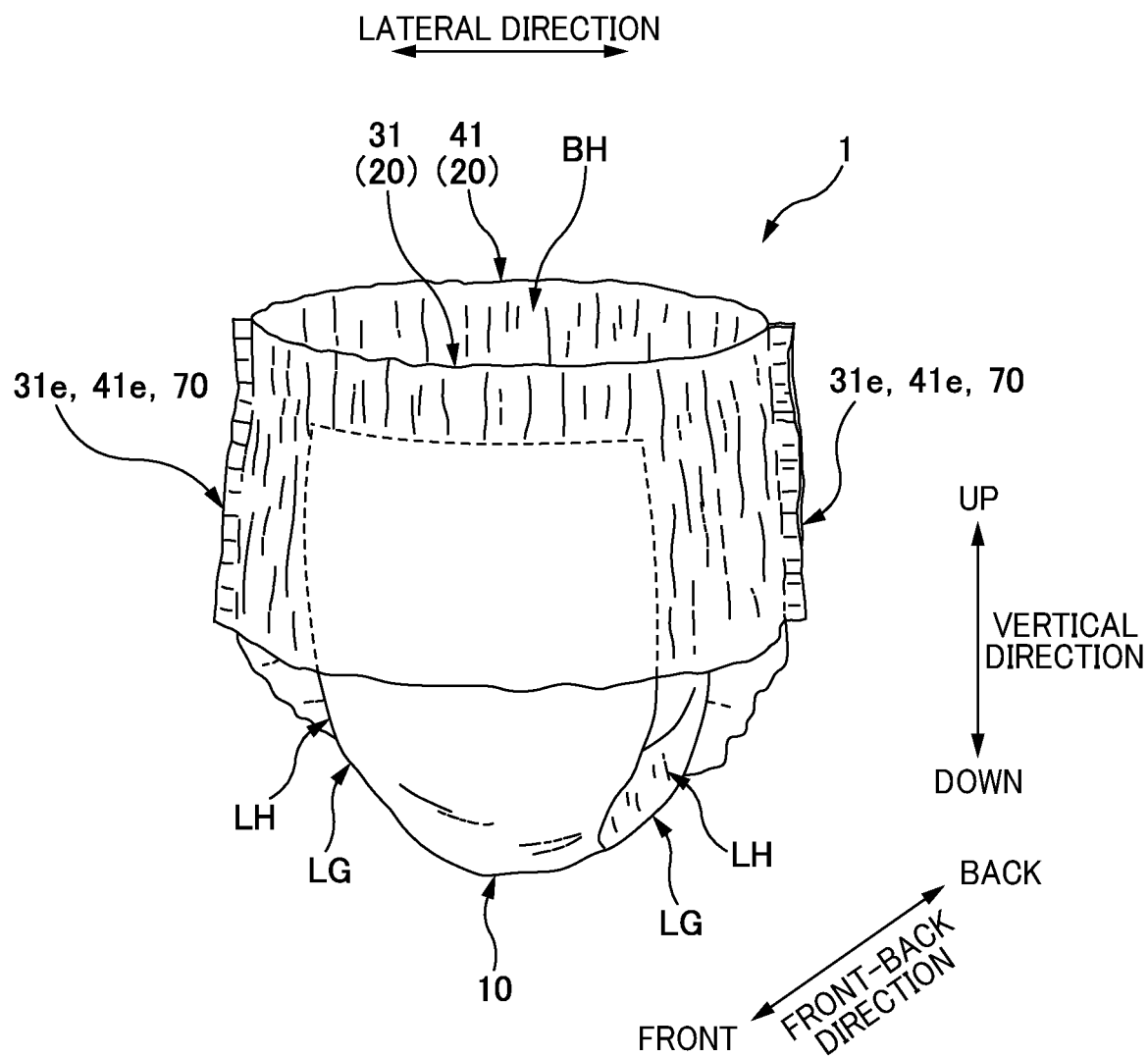
FIG. 1 is a schematic perspective view of a diaper.

At least the following matters will be clear with the description of this specification and the attached drawing.

A stretchable sheet including: a first sheet; a second sheet that is joined to the first sheet by a plurality of welded portions; and an elastic member that is provided between the first sheet and the second sheet, the elastic member being capable of stretching and contracting in a continuous direction in which the elastic member continues, the plurality of the welded portion being located on both sides of the elastic member in the intersecting direction that intersects with the continuous direction, a plurality of welded portion pairs being provided in which the elastic member is sandwiched and that restricts a position of the elastic member in the intersecting direction with respect to the first sheet and the second sheet, the elastic member having a damaged portion where a part of a surface of the elastic member is damaged, the welded portion pair having a first welded portion pair and a second welded portion pair that is located adjacent to the first welded portion pair in the continuous direction, at least one of the damaged portion being provided between the first welded portion pair and the second welded portion pair in the continuous direction.

According to such a stretchable sheet, the damaged portion, which is formed in the elastic member, is likely to be caught up in either of the first welded portion pair and the second welded portion pair. This makes the elastic member less likely to relatively move with respect to the welded portion pairs in the continuous direction, suppressing the displacement of the elastic member, and the like. As a result, the elastic member is firmly attached between the first sheet and the second sheet, and the stretchability of the stretchable sheet is less likely to deteriorate.

In such a stretchable sheet, when the elastic member being in a stretched state, an outer diameter of the elastic member in the damaged portion may be larger than a gap of the welded portion pair in the intersecting direction.

According to such a stretchable sheet, regardless of whether the stretchable sheet contracts or stretches, the damaged portion of the elastic member is caught in the welded portion pair, and thereby the elastic member is less likely to come off from the welded portion pair, making it likely to maintain a good stretchability.

In such a stretchable sheet, the elastic member may be an aggregation of a plurality of elastic fibers.

According to such a stretchable sheet, even if some of the plurality of elastic fibers are severed at the damaged portion, the effect is less likely to affect the other elastic fibers. Therefore, it is likely to prevent the entirety of elastic member (all the elastic fibers) from being severed, and it is possible to make the stretchability less likely to deteriorate.

In such a stretchable sheet, a plurality of the elastic fibers may be damaged in the damaged portion.

According to such a stretchable sheet, as the damaged elastic fibers increases, the outer diameter of the elastic member in the damaged portion is made more likely to be thicker due to the contraction of the damaged elastic fibers, and the elastic member is made more likely to be caught by the welded portion pair. This makes the elastic member less likely to come off from the welded portion pair, making it possible to make the stretchability less likely to deteriorate.

In such a stretchable sheet, with respect to the continuous direction, in a portion of the elastic member where the damaged portion is formed, a number of damaged ones of the elastic fibers may be smaller than a number of undamaged ones of the elastic fibers.

According to such a stretchable sheet, in the portion where the damaged portion is formed, the fewer the number of damaged elastic fibers, the stronger the elastic member is likely to be. This makes the elastic member less likely to be severed as a whole, and the stretchability is less likely to deteriorate.

In such a stretchable sheet, in the damaged portion, the elastic member may have a portion where a damaged elastic fiber of the elastic fibers is peeled off from an undamaged elastic fiber of the elastic fibers.

According to such a stretchable sheet, if the damaged elastic fiber is peeled off from the undamaged elastic fiber, the damaged elastic fiber is likely to contract on its own. Therefore, the outer diameter of the elastic member in the damaged portion becomes thicker, making it likely to get caught by the welded portion pair. This makes the elastic member less likely to come off from the welded portion pair, making it possible to make the stretchability less likely to deteriorate.

In such a stretchable sheet, the elastic member may be twisted in the continuous direction.

According to such a stretchable sheet, fibers of the sheet member (nonwoven fabric) which constitutes the first sheet and the second sheet get entangled or caught in the twisted portions of the elastic member, and this makes the frictional force between the elastic member and the sheet member make it likely to increase. This prevents the elastic member from being displaced in the continuous direction, making the stretchability less likely to deteriorate.

In such a stretchable sheet, the welded portion pair may include a third welded portion pair and a fourth welded portion pair that are different from the first welded portion pair and the second welded portion pair and that are adjacent to each other in the continuous direction, and the damaged portion may not be provided between the third welded portion pair and the fourth welded portion pair in the continuous direction.

According to such a stretchable sheet, there are cases in which the damaged portion is not provided between some pairs of the welded portion pairs that are located adjacent in the continuous direction, and this makes it possible to decrease the probability of the elastic member being cut, compared to the case where the damaged portion is provided between all pairs of the welded portion pairs. This makes it likely to suppress the stretchability from deteriorating.

In such a stretchable sheet, a number of the welded portion pairs that are located between a one-side end and an other-end end of the elastic member in the continuous direction may be greater than a number of the damaged portions that are located between the one-side end and the other-end end of the elastic member in the continuous direction.

According to such a stretchable sheet, for each of the plurality of elastic members, among locations between pairs of the welded portion pairs that are located adjacent in the continuous direction, some are ones where the damaged portion is present and the others are ones where the damaged portion is not present. Therefore, for each of the elastic members, the displacement in the continuous direction and the like is suppressed, and the elastic member is less likely to be cut. This makes the stretchable sheet as a whole possible for the stretchability to be less likely to deteriorate.

In such a stretchable sheet, the stretchable sheet may have a thickness direction that intersects the continuous direction and the intersecting direction, and the damaged portion may not have a portion that penetrates the first sheet and the second sheet in the thickness direction.

According to such a stretchable sheet, the cutting point of the elastic member are less likely to be seen from the outside, and the texture is less likely to deteriorate. This makes it possible to prevent the user from feeling anxiety or discomfort.

In such a stretchable sheet, the underpants-shaped absorbent article may have a vertical direction, a lateral direction, and a front-back direction that intersect with each other, the underpants-shaped absorbent article may comprise: an absorbent main body; and a waist portion in which a front waist portion and a back waist portion are joined by a side-joining-portion region in two lateral ends, at least one of the front waist portion and the back waist portion may have the stretchable sheet in at least a partial region, the lateral direction may be a direction that conforms to the continuous direction, the vertical direction may be a direction that conforms to the intersecting direction, and when the underpants-shaped absorbent article in a stretched state is viewed in the front-back direction, at least one of the elastic member may be located overlapping with the side-joining-portion region.

According to such an underpants-shaped absorbent article, in a lateral end (the side-joining-portion region), the elastic member is likely to be fixed in a state of being sandwiched between the first sheet and the second sheet in the thickness direction. Therefore, during usage of the underpants-shaped absorbent article, rubber coming off is less likely to occur, and it is possible to prevent the stretchability of the waist portion from deteriorating to cause the deterioration of the fit.

In such a stretchable sheet, the side-joining-portion region may have a plurality of the side joining portions that are lined up at a predetermined interval in the vertical direction, and an average length of the welded portions in the lateral direction may be smaller than an average length of the side joining portions in the lateral direction.

According to such an underpants-shaped absorbent article, if the area (width) of the welded portions is large, this makes texture around the waist hard during usage, causing a risk of making the wearer likely to feel discomfort. On the other hand, by making the length of the welded portions in the lateral direction smaller than the length of the side joining portion in the lateral direction, it is possible to make the user less likely to feel unpleasantness and discomfort compared to the opposite case.

In such a stretchable sheet, a center line of a portion of the elastic member that is located in the side-joining-portion region located on a one side in the lateral direction may be inclined with respect to a center line of a portion of the elastic member that is located between the first welded portion pair and the second welded portion pair.

According to such an underpants-shaped absorbent article, a force that causes rubber coming off is less likely to act directly on the portion of the elastic member that is located in the side-joining-portion region (the force is more likely to be dispersed), and it is possible to suppress the coming off of the elastic member from the side-joining-portion region.

In such a stretchable sheet, the side joining portion may have a first side joining portion and a second side joining portion that are adjacent in the vertical direction, and in the side-joining-portion region, a part of the elastic member may be sandwiched in the vertical direction between the first side joining portion and the second side joining portion.

According to such an underpants-shaped absorbent article, by being sandwiched in the vertical direction between the first side joining portion and the second side joining portion, it increases the frictional force between the elastic member and the pair of the upper and lower side joining portions (the first side joining portion and the second side joining portion). Therefore, the elastic member is prevented from coming off from the side-joining-portion region, and the stretchability of the waist portion is less likely to deteriorate.

In such a stretchable sheet, in the side-joining-portion region, a part of the elastic member may be sandwiched between the first sheet and the second sheet due to the side joining portion.

According to such an underpants-shaped absorbent article, in the side joining portion, a part of the elastic member is strongly sandwiched between the first sheet and the second sheet. Therefore, the elastic member is prevented from coming off from the side-joining-portion region, making the stretchability of the waist portion less likely to deteriorate.

In such a stretchable sheet, in at least one of the front waist portion and the back waist portion, the underpants-shaped absorbent article may have a discontinuous portion where the elastic member is discontinuous in the lateral direction.

According to such an underpants-shaped absorbent article, in the portion where the elastic member is cut and becomes discontinuous, the elastic member contracts and becomes thicker in outer diameter, so that the elastic member is more likely to be caught by the welded portion pair. This makes it likely to suppress rubber coming off, etc., making the stretchability less likely to deteriorate. Furthermore, providing the discontinuous portion makes it possible to partially adjust the strength of stretching/contracting of the elastic member, enabling to improve the fit of the underpants-shaped absorbent article.

In such a stretchable sheet, the underpants-shaped absorbent article may have a portion where at least one pair of the welded portion pair and the absorbent main body overlap when viewed in the front-back direction.

According to such an underpants-shaped absorbent article, in the region which overlaps the absorbent main body, which has high stiffness, the waist portion is less likely to deform, and the distance in the vertical direction between the welded portion pair is likely to maintain. This makes the damaged portion of the elastic member likely to be caught up in the welded portion pair, making it less likely to cause the displacement in the continuous direction.

In such a stretchable sheet, a post-handling tape may be provided on a non-skin-side surface of the back waist portion, the post-handling tape being used when disposing of the underpants-shaped absorbent article after use, and the underpants-shaped absorbent article may have a portion where at least one pair of the welded portion pair and the post-handling tape overlap when viewed in the front-back direction.

According to such an underpants-shaped absorbent article, in the region which overlaps the post-handling tape, which has high stiffness, the waist portion is less likely to deform, and the distance in the vertical direction between the welded portion pair is likely to maintain. This makes the damaged portion of the elastic member likely to be caught up in the welded portion pair, making it less likely to cause the displacement in the continuous direction.

In such a stretchable sheet, the underpants-shaped absorbent article may have a main-body joining portion that connects the absorbent main body and the waist portion, and the underpants-shaped absorbent article may have a portion where at least one pair of the welded portion pair and the main-body joining portion overlap when viewed in the front-back direction.

According to such an underpants-shaped absorbent article, the stiffness of the waist portion is higher in the portion where the main-body joining portion is provided compared to the portions where the main-body joining portion is not provided. Therefore, the distance in the vertical direction between with the welded portion pair that are arranged overlapping the main-body joining portion is likely to maintain, and the damaged portion of the elastic member is likely to be caught in the welded portion pair. This makes it likely to prevent the deterioration of the stretchability of the waist portion.

In such a stretchable sheet, at least two of the welded portion pairs may overlap the main-body joining portion with respect to the vertical direction.

According to such an underpants-shaped absorbent article, it is likely to maintain the relative positions of at least two welded portion pairs with respect to the vertical direction, making it less likely to cause the displacement of the elastic member in the vertical direction. Therefore, in stretchability due to the elastic member, a difference between the upper side and the lower side in the vertical direction is less likely to occur, enabling to make it less likely to cause distortion when the waist portion stretches and contracts.

In such a stretchable sheet, at least two of the welded portion pairs may overlap the main-body joining portion with respect to the lateral direction.

According to such an underpants-shaped absorbent article, the damaged portion of the elastic member is more likely to be caught in at least two welded portion pairs in the lateral direction. This makes it more likely to suppress the displacement of the elastic member in the continuous direction, enabling to make the stretchability of the waist portion to deteriorate.

A method for manufacturing a stretchable sheet, the stretchable sheet including: a first sheet; a second sheet that is joined to the first sheet by a plurality of welded portions; and an elastic member that is provided between the first sheet and the second sheet, the elastic member being capable of stretching and contracting in a continuous direction in which the elastic member continues, the plurality of the welded portion being located on both sides of the elastic member in the intersecting direction that intersects with the continuous direction, a plurality of welded portion pairs being provided in which the elastic member in a state of contracting in the continuous direction is sandwiched and that restricts a position of the elastic member in the intersecting direction with respect to the first sheet and the second sheet, the method including: a transporting step for transporting a continuous body of the first sheet, a continuous body of the second sheet, and a continuous body of the elastic member in a direction of transport, the direction of transport corresponding to the continuous direction, the continuous body of the first sheet, the continuous body of the second sheet, and the continuous body of the elastic member being continuous in the continuous direction; and a joining step for joining the continuous body of the first sheet and the continuous body of the second sheet, by arranging a plurality of the continuous bodies of the elastic members side by side in a intersecting direction between the continuous body of the first sheet and the continuous body of the second sheet, and by subsequently forming a plurality of the welded portion pair so that each of the continuous bodies of the elastic members is sandwiched from both sides in the intersecting direction, the continuous bodies of the elastic members being in a state of being stretched in the direction of transport, the intersecting direction intersecting the direction of transport, when forming the welded portion pair in the joining step, forming a damaged portion where a part of a surface of the continuous body of the elastic member is damaged, and joining the continuous body of the first sheet and the continuous body of the second sheet so that at least one of the damaged portion is arranged between a first welded portion pair and a second welded portion pair that are adjacent to each other in the continuous direction.

According to such a manufacturing method of the stretchable sheet, the damaged portion, which has been formed in the elastic member, is likely to be caught in either of the first welded portion pair and the second welded portion pair, and this makes the elastic member less likely to move with respect to the welded portion pair in the continuous direction, suppressing the displacement of the elastic member, and the like. As a result, the elastic member is firmly attached between the first sheet and the second sheet, and the stretchable sheet can be realized in which the stretchability is less likely to deteriorate.

A stretchable sheet including: a first sheet; a second sheet that is joined to the first sheet by a plurality of welded portions; and an elastic member that is provided between the first sheet and the second sheet, the elastic member being capable of stretching and contracting in a continuous direction in which the elastic member continues, the plurality of the welded portion being located on both sides of the elastic member in the intersecting direction that intersects with the continuous direction, a plurality of welded portion pairs being provided in which the elastic member is sandwiched and that restricts a position of the elastic member in the intersecting direction with respect to the first sheet and the second sheet, at least some of a plurality of the elastic members being colored in a different color between the first sheet and the second sheet, in the continuous direction, letting S be a length of the welded portion pair, letting N be a distance between inner ends of two welded portion pairs that are in a stretched state and adjacent to each other, letting X be a value obtained by dividing a length of the stretchable sheet in the stretched state by a length of the stretchable sheet in a natural state, the stretchable sheet having a portion that satisfies either one of following Equation (1) and Equation (2).

$$X \leq 2 \quad (1)$$

$$S > \frac{N}{2} - \frac{N}{X} \quad (2)$$

According to such a stretchable sheet, in a portion that satisfies either one of Equation (1) and Equation (2), this makes it likely to prevent the welded portion pair from being completely covered with fallen wrinkles compared to the case where Equation (1) and Equation (2) are not satisfied. Therefore, at least a part of a portion of the colored elastic member that is sandwiched between the welded portion pair is made likely to be seen from the outside in the thickness direction, enabling to make the user likely to recognize that, in the stretchable sheet, the stretchability due to the elastic members act.

In such a stretchable sheet, the welded portion pair may have a first welded portion pair that is located on a one side in the continuous direction, and a second welded portion pair that is located on another side of and adjacent to the first welded portion pair, the first welded portion may have one or more notched portion inbetween in the continuous direction, the first welded portion pair may be divided by the notched portion, and letting S2 be a value in the continuous direction obtained by subtracting a length of a located-farthest-on-one-side portion among the divided portions of the first welded portion pair from the length of the first welded portion pair, the stretchable sheet may further satisfy a following Equation (3).

$$S2 > \frac{N}{2} - \frac{N}{X} \quad (3)$$

According to such a stretchable sheet, even in the case where the welded portion pair (first welded portion pair) has been divided by the notched portion in the continuous direction, compared to the case where the condition of Equation (3) is not satisfied, further satisfying Equation (3) makes it likely to visually recognize the elastic member that is sandwiched between the welded portion pair (outer first welded portion pair), which is located farthest on the one side in the continuous direction among the divided portions of the first welded portion pair. This can make the user likely to recognize that the stretchability due to the elastic member acts.

In such a stretchable sheet, the stretchable sheet may further satisfy a following Equation (4).

$$S > \frac{N}{2} - \frac{N}{2X} \quad (4)$$

According to such a stretchable sheet, even if the wrinkles formed in the first sheet etc. are the largest, further satisfying Equation (4) makes it likely to visually recognize the elastic member that is sandwiched between the welded portion pair, compared to the case where the condition of Equation (4) is not satisfied. This can make the user likely to recognize that the stretchability due to the elastic member acts.

In such a stretchable sheet, the elastic member may include uncolored ones, and in the continuous direction, a total length of the welded portion pairs provided in a region where the elastic member that is colored is arranged may be longer than a total length of the welded portion pairs provided in a region where the elastic member that is not colored is arranged.

According to such a stretchable sheet, the wrinkles formed in the region where colored elastic member is arranged are smaller than the wrinkles formed in the region where uncolored elastic member is arranged. As a result, the visibility of the elastic member becomes higher in the region where the colored elastic member is arranged, enabling to make the user likely to recognize the stretchability.

In such a stretchable sheet, a pitch of the elastic members in the intersecting direction in the region where the elastic member that is colored is arranged
  may be smaller than
    a pitch of the elastic members in the intersecting direction in the region where the elastic member that is not colored is arranged.

According to such a stretchable sheet, by making the pitch of the colored elastic members in the intersecting direction smaller than the pitch of the uncolored elastic members in the intersecting direction, it is possible to make the visibility of the colored elastic members higher than the visibility of the uncolored elastic members. This makes the user likely to recognize the stretchability in the region where the colored elastic members are arranged.

In such a stretchable sheet, either of the first sheet and the second sheet may be a nonwoven fabric sheet that includes titanium oxide, and a content rate of titanium oxide of the elastic member may be less than 3.0%.

According to such a stretchable sheet, in order to improve the aesthetics of a nonwoven fabric sheet, it is known to color a nonwoven fabric sheet white as a whole using fibers kneaded with titanium oxide. When producing the stretchable sheet by making the elastic members sandwiched between such a nonwoven fabric sheet, including titanium oxide in the elastic members decreases the visibility of the elastic members through the nonwoven fabric sheet because the elastic members is made cloudy. By making the content of titanium oxide less than 3.0%, the visibility of the colored elastic member improves, enabling to make the user likely to recognize the stretchability.

First Example

Basic Configuration of Underpants-Shaped Disposable Diaper

Figure 2:
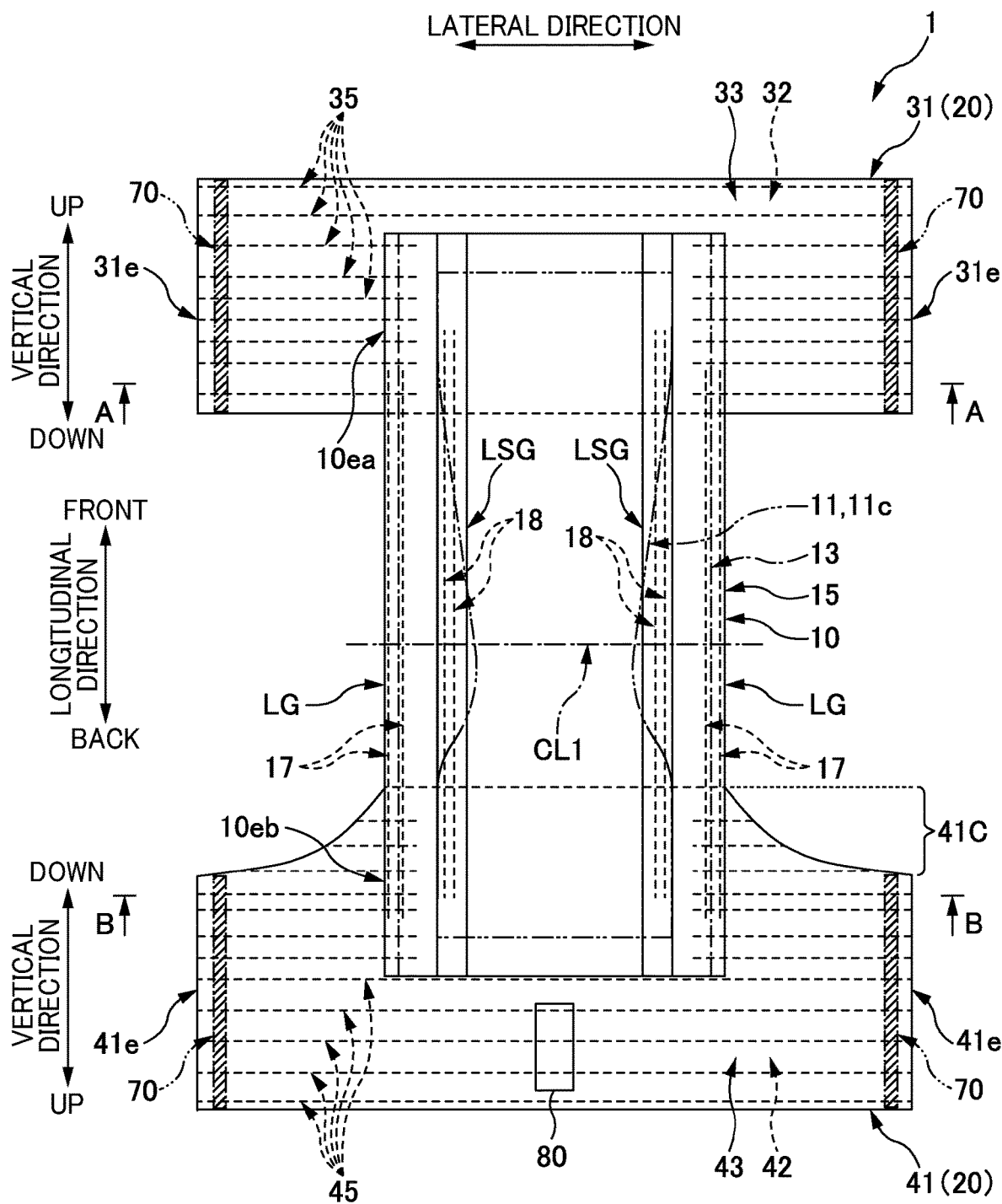
FIG. 2 is a schematic plan view of the diaper in an unfolded and stretched state when viewed from a wearer's skin side.
Figure 3:
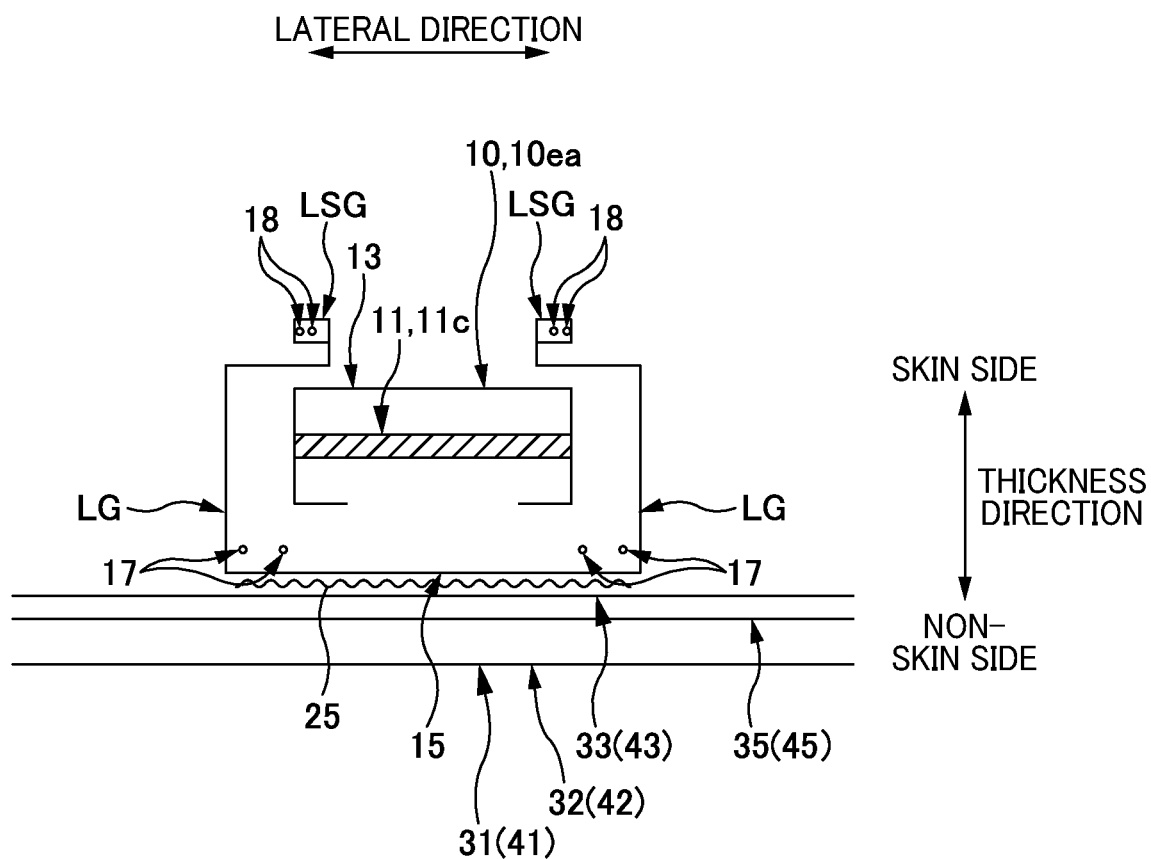
FIG. 3 is a sectional view taken along line A-A in FIG. 2, and also a sectional view taken along line B-B in FIG. 2.

An underpants-shaped disposable diaper 1 (hereinafter also referred to as "diaper 1") will be described by way of example of underpants-shaped absorbent article in which a stretchable sheet according to one or more embodiments is used. In the diaper 1, the stretchable sheet is used as a band member around the waist (the front waist portion 31 and the back waist portion 41, which will be described later). FIG. 1 is a schematic perspective view of the diaper 1. FIG. 2 is a schematic plan view of the diaper 1 in an unfolded and stretched state when viewed from a wearer's skin side. FIG. 3 is a sectional view taken along line A-A in FIG. 2, and also a sectional view taken along line B-B in FIG. 2.

This diaper 1 in an underpants-shaped state before wearing as shown in FIG. 1 has three directions that intersect with each other, namely a "vertical direction", a "lateral direction", and a "front-back direction". With respect to the vertical direction, the upper side corresponds to the waist opening side of the wearer, and the lower side corresponds to the crotch side of the wearer. Further, with respect to the front-back direction, the front side corresponds to the stomach side of the wearer, and the back side corresponds to the back side of the wearer.

In the underpants-shaped state in FIG. 1, the diaper 1 includes an absorbent main body 10 and a waist portion 20. The waist portion 20 includes: a front waist portion 31 which has stretchability along the lateral direction; and a back waist portion 41 which has stretchability in the lateral direction, and which is located on the back side of the front waist portion 31 and forms the waist opening BH together with the front waist portion 31 in the upper side in the vertical direction. The absorbent main body 10 is provided as a crotch portion that is located between the front waist portion 31 and the back waist portion 41.

Further, the lateral end portions 31e and 31e of the front waist portion 31 and the corresponding lateral end portions 41e and 41e of the back waist portion 41 are joined in the side-joining-portion regions 70 which extend in the vertical direction. Thus, the front waist portion 31 and the back waist portion 41 cooperate with the absorbent main body 10 to form leg openings LH and LH in the lower side and on both lateral sides.

Here, the "unfolded state" refers the following state: the front waist portion 31 and the back waist portion 41 are separated by releasing the joining of the aforementioned side-joining-portion regions 70 that are provided in the diaper 1 in the underpants-shaped state shown in FIG. 1 on both lateral sides, and in addition the diaper 1 is unfolded on a flat surface by spreading open in the vertical direction. In addition, the "stretched state" refers to the state in which the product (diaper 1) has been stretched to the extent that wrinkles are eliminated, or more specifically, the state in which the diaper 1 is stretched such that the dimensions of constituent members of the diaper 1 (e.g., the absorbent main body 10, the front waist portion 31, etc.) match or are closer to the dimensions of the members on their own.

In the unfolded state, the diaper 1 has three directions that intersect with each other: a "longitudinal direction," a "lateral direction," and a "thickness direction (the direction passing through the paper surface in FIG. 2)". Note that the longitudinal direction conforms to the vertical direction mentioned above. The one side in the longitudinal direction corresponds to the front side, and the other side corresponds to the back side. Further, the outside in the longitudinal direction corresponds to the upper side in the vertical direction (waist opening side), and the inside in the longitudinal direction corresponds to the lower side (crotch side) in the vertical direction. Since the longitudinal direction and the vertical direction are directions that resemble each other, for the sake of convenience hereinafter, the vertical direction will sometimes be used in place of the longitudinal direction in the unfolded state as well. Furthermore, the lateral direction is synonymous with the lateral direction in the previously described underpants-shaped state. Further, with respect to the thickness direction, the one side corresponds to the skin side that comes into contact with the wearer's body, and the other side corresponds to the opposite non-skin side.

In the unfolded state shown in FIG. 2, the front waist portion 31 is arranged extending in the lateral direction, and the back waist portion 41 is arranged extending in the lateral direction at a position that is separated from the front waist portion 31 by a predetermined distance in the longitudinal direction. The absorbent main body 10 spans along the longitudinal direction between the front waist portion 31 and the back waist portion 41, and the longitudinal end portions 10ea and 10eb of the absorbent main body 10 (i.e., the front upper end portion 10ea and the back upper end portion 10eb in the underpants-shaped state) are respectively joined and fixed to the closest waist portions 31 and 41, thus forming a substantially H-like outer shape in a plan view. The diaper 1 in this state is folded one time at a folding position that is at the predetermined longitudinal position CL1 of the absorbent main body 10 (corresponding to the longitudinal central position of the diaper 1), and the lateral end portions 31e and 41e of the waist portions 31 and 41, which face each other in the folded state, are joined to each other in the above-mentioned side-joining-portion regions 70. Accordingly, the waist portions 31 and 41 become connected to each other in a ring shape, thus obtaining the diaper 1 in the underpants-shaped state in which the waist opening BH and a pair of leg openings LH and LH are formed as shown in FIG. 1.

Absorbent Main Body 10

The absorbent main body 10 has a substantially rectangular shape in a plan view in the unfolded state in FIG. 2. The longitudinal direction of the absorbent main body 10 conforms to the longitudinal direction of the diaper 1. Also, as shown in FIG. 3, the absorbent main body 10 includes: an absorbent body 11; a liquid-permeable top sheet 13 that covers the absorbent body 11 from the skin side and forms the skin-side surface of the absorbent main body 10; and a liquid-impermeable back sheet 15 that covers the absorbent body 11 from the non-skin side and forms the non-skin-side surface of the absorbent main body 10.

The absorbent body 11 has a liquid-absorbent absorbent core 11c, and a core-wrapping sheet (not shown) that covers the outer circumferential surface of the core 11c. The absorbent core 11c is a molded body that is made of a liquid absorbent material, such as pulp fiber and superabsorbent polymer, into a substantially hourglass shape in a plan view, as one example of a predetermined shape. The core-wrapping sheet can made of a liquid-permeable sheet such as tissue paper or nonwoven fabric, but the core-wrapping sheet is not required to be provided. Further, the absorbent core 11c is not limited to having the above-described substantially hourglass shape in a plan view, and may have any other shape.

The top sheet 13 is a liquid-permeable soft sheet made of nonwoven fabric or the like. The back sheet 15 is also a liquid-impermeable soft sheet. One example of the back sheet 15 is a two-layer structure laminate sheet including: a liquid-impermeable leak-proof sheet made of a polyethylene film or a polypropylene film; and an exterior sheet that is made of nonwoven fabric and is affixed to the non-skin side of the leak-proof sheet.

As shown in FIG. 2, at least the back sheet 15 is a sheet having a planar size according to which it projects from the absorbent body 11 in the longitudinal direction and the lateral direction. Leg gathers LG that stretch and contract in the longitudinal direction are formed in the portions that protrude in the lateral direction. Specifically, elastic strings 17 that serve as elastic members and extend in the longitudinal direction are fixed in the protruding portion in a state of being stretched in the longitudinal direction, thus forming the stretchable leg gathers LG in these portions.

Further, as shown in FIGS. 2 and 3, the absorbent main body 10 has barrier cuffs LSG as leak-proof wall portions in the lateral end portions for the purpose of preventing side leakage. Specifically, in the lateral end portions of the absorbent main body 10, a configuration is provided in which elastic strings 18 serving as elastic members and extending in the longitudinal direction are attached, in a state of being stretched in the longitudinal direction, to sheet-like portions that will form the barrier cuffs LSG.

Waist Portions 31 and 41

As shown in FIG. 2, the front waist portion 31 is a sheet member that has a substantially rectangular shape in a plan view and is constituted by a first sheet 32 and a second sheet 33 which are stacked in the thickness direction. Specifically, as shown in FIG. 3, the first sheet 32 and the second sheet 33 are overlaid in the thickness direction. And, a pair of facing surfaces that faces each other are joined to each other by a plurality of welded portions 50, 50, . . . that are arranged discretely spacing in the vertical direction and the lateral direction, as shown in later-described FIG. 4. As shown in FIG. 2, the front waist portion 31 is arranged so as to protrude out from the absorbent main body 10 on two lateral sides, and is overlaid on and joined to the non-skin side of the front end portion (front upper end portion) 10ea of the absorbent main body 10.

Similarly to the front waist portion 31, the back waist portion 41 is a sheet member made of a first sheet 42 and a second sheet 43 which are stacked in the thickness direction. Specifically, as shown in FIG. 3, the first sheet 42 and the second sheet 43 are overlaid in the thickness direction. And a pair of facing surfaces that faces each other are joined to each other by a plurality of welded portions 50, 50, . . . that are arranged discretely spacing in the vertical direction (longitudinal direction) and the lateral direction, similar to the case of the front waist portion 31 in FIG. 4. As shown in FIG. 2, the back waist portion 41 is arranged so as to protrude out from the absorbent main body 10 on two lateral sides, and is overlaid on and joined to the non-skin side of the back end portion (back upper end portion) 10eb of the absorbent main body 10.

Note that, the back waist portion 41 has a substantially trapezoidal buttocks cover 41c as shown in FIG. 2, below the side-joining-portion region 70 in the vertical direction. The buttocks cover 41c is a portion that broadly covers the wearer's buttocks when the diaper 1 is put on.

Further, in this example, spunbond nonwoven fabric is used for both of the first sheet 32 (42) and the second sheet 33 (43) pertaining to the front waist portion 31 (41). However, there is no limitation whatsoever to this, and it is possible to use various other types of nonwoven fabric such as SMS (spunbond/meltblown/spunbond) nonwoven fabric. Further, in this example, standalone fibers made of polypropylene (PP), which is a representative example of thermoplastic resin, may be used as the constituent fibers of the nonwoven fabric, but there is no limitation whatsoever to this. For example, standalone fibers made of another thermoplastic resin such as polyethylene (PE) may be used, and composite fibers that have a sheath/core structure and are made of PE and PP or the like may be used.

Specific Configuration of Front Waist Portion 31 (41)

Next, the specific configuration of the front waist portion 31 and the back waist portion 41, which are formed using the stretchable sheet according to one or more embodiments, will be described. As mentioned above, the front waist portion 31 and the back waist portion 41 of one or more embodiments have substantially the same configuration. Therefore, when the contents described below is the same for both the front waist portion 31 and the back waist portion 41, only the front waist portion 31 will be described as a representative for both. Regarding the back waist portion 41, the reference signs of its components and the like corresponding to those of the front waist portion 31 will be indicated by blanketing as necessary, and the concrete description will be omitted.

Figure 4:
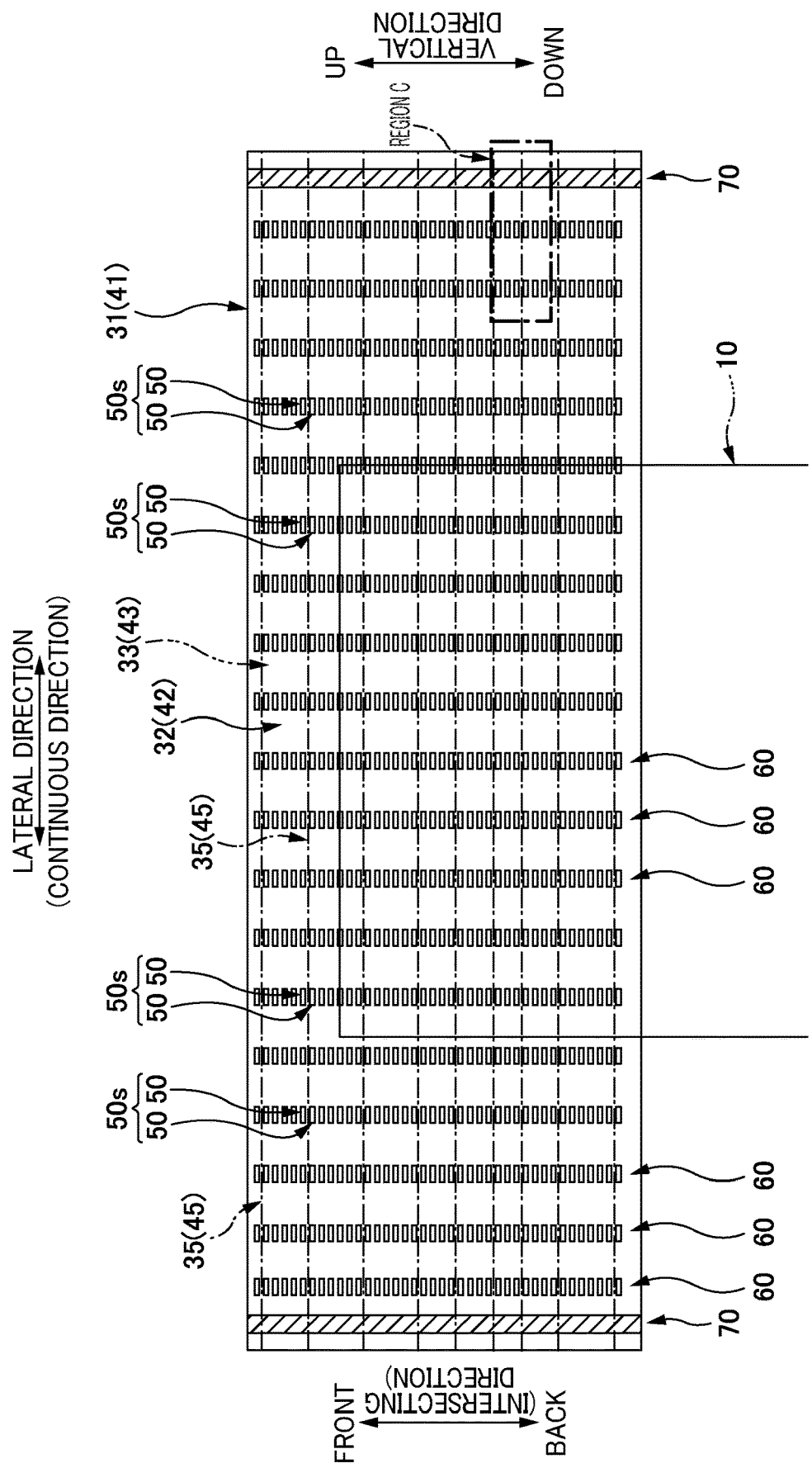
FIG. 4 is a schematic plan view of a front waist portion (stretchable sheet) in the unfolded and stretched state when viewed from a non-skin side.
Figure 5:
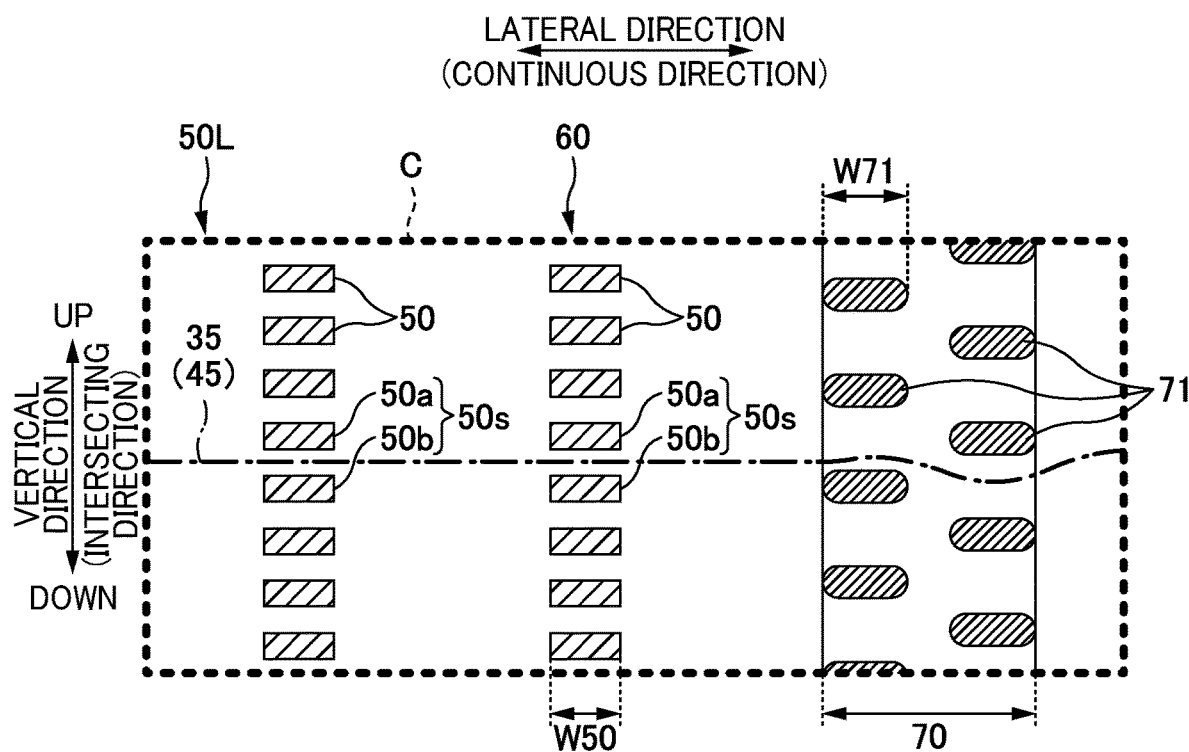
FIG. 5 is an enlarged view of a region in FIG. 4.

FIG. 4 is a schematic plan view of the front waist portion 31 (stretchable sheet) in the unfolded and stretched state when viewed from the non-skin side. In addition, in FIG. 4, the front waist portion 31 (41) is shown as a constituent member of the diaper 1, but the waist portions 31 and 41 can also be applied to uses other than the diaper 1 as a stretchable sheet. FIG. 5 is an enlarged view of a region C in FIG. 4.

As shown in FIG. 4, in the first sheet 32 (42) and the second sheet 33 (43) pertaining to the front waist portion 31 (41), a plurality of waist elastic members 35, 35, . . . (45, 45, . . . ), which are elastic strings etc. that can stretch and contract in the lateral direction, are inserted side-by-side spacing in the vertical direction between a pair of facing surfaces that face each other. And the waist elastic members 35, 35, . . . (45, 45, . . . ) are attached to the sheets 32 and 33 (42 and 43) with use of the above-mentioned welded portions 50, 50, . . . . Accordingly, the front waist portion 31 (41) is given stretchability in the lateral direction. Also, the above-mentioned welded portions 50, 50 . . . not only have a function of joining the pair of facing surfaces of the first sheet 32 (42) and the second sheet 33 (43) to each other, but also have a function of attaching the waist elastic members 35 (45) to the first sheet 32 (42) and the second sheet 33 (43).

Hereinafter, the direction in which each of the waist elastic members 35, 35, . . . continues is also referred to as a "continuous direction", and the direction which intersects the continuous direction is also referred to as an "intersecting direction". In one or more embodiments, as shown in FIG. 4, the continuous direction is a direction that conforms to the lateral direction of diaper 1, and the intersecting direction is a direction that conforms to the longitudinal direction (the vertical direction) of diaper 1.

In the front waist portion 31 (41) of one or more embodiments, the plurality of welded portions 50, 50, . . . are lined up side-by-side in the vertical direction (intersecting direction) at a predetermined gap, thereby forming a welded portion row 60 extending in the vertical direction (intersecting direction). And a plurality of the welded portion rows 60 are provided at intervals in the lateral direction. In the example of FIG. 4, the welded portion rows 60 are each arranged straight in the vertical direction, but the welded portion rows 60 may meander with respect to the lateral direction. In other words, the plurality of welded portions 50 that constitute one welded portion row 60 may be located at different positions with respect to the lateral direction (see FIG. 14, which will be described later).

As shown in FIG. 4, the plurality of welded portions 50 are provided at predetermined intervals in the vertical direction and in the lateral direction, and this makes it possible to suppress deterioration of texture of the diaper 1 being put on while maintaining the flexibility of the front waist portion 31 (41). Assuming that a line-shaped welded portion extending continuously in the vertical direction or in the lateral direction is formed. In a portion where the welded portion is formed, nonwoven fabric becomes stiff, and, it is more likely to suppress deformation of nonwoven fabric in a direction in which the line-shaped welded portion extends. In contrast, the welded portion row 60 in which the small welded portions 50 are dispersed as shown in FIG. 4 makes it possible to provide a flexible sheet member which makes a user (wearer) of diaper 1 less likely to feel curing of nonwoven fabric and makes it less likely to inhibit deformation of nonwoven fabric in the vertical direction and in the lateral direction.

In the front waist portion 31 (41), of the plurality of welded portions 50 in the welded portion row 60, a waist elastic member 35 (hereinafter simply referred to as elastic member 35 (45)) is sandwiched in the vertical direction between two welded portions 50 and 50 adjacent in the vertical direction, and thereby that elastic member 35 is attached to the front waist portion 31 (41). Specifically, a pair of welded portions 50 and 50 respectively located on both sides of the elastic member 35 in the vertical direction (intersecting direction) serve as a welded portion pair 50s, and the elastic member 35 is attached by the welded portion pair 50s. Hereinafter, as shown in FIG. 5, among the pair of the welded portions 50 and 50 that constitute the welded portion pair 50s, the welded portion 50 which is located on the one side in the intersecting direction (upper side in the vertical direction) across the elastic member 35 is referred to as an upper welded portion 50a, and the welded portion 50 which is located on the other side in the intersecting direction (lower side in the vertical direction) across the elastic member 35 (45) is referred to as a lower welded portion 50b. The mechanism by which the elastic member 35 (45) is attached by the welded portion pair 50s will be described later.

Further, the side-joining-portion regions 70 are provided at the lateral end portions 31e of the front waist portion 31, for connecting with the end portion 41e of the back waist portion 41. Each side-joining-portion region 70 is formed by a plurality of the dispersed side joining portions 71, 71, . . . . In FIG. 5, a plurality of oval-shaped side joining portions 71 are arranged at intervals in the vertical direction (intersecting direction) and in the lateral direction (continuous direction). However, the shape and arrangement of the side joining portions 71 can be changed as appropriate. Each of the side joining portions 71 can be formed using welding means such as ultrasonic welding, heat welding, and high-frequency sealing, and non-heating pressurizing means, for example. Furthermore, in the diaper 1, at least some of the elastic members 35 are located overlapping the side-joining-portion regions 70 with respect to the lateral direction (see FIG. 5).

In addition, in FIG. 4, the welded portion rows 60 are formed across the entire front waist portion 31 (41), and the elastic members 35 (45) are arranged continuously from the one-side end to the other-side end in the lateral direction (continuous direction). That is, the entire front waist portion 31 (41) is formed by the stretchable sheet, which can stretch and contract in the lateral direction (continuous direction) due to the elastic members 35 (45). However, the configuration of the front waist portion 31 (41) is not limited to this. For example, a configuration in which the stretchable sheet is used only in some regions of the front waist portion 31 (41), or a configuration in which the stretchability does not exhibit in some regions may be employed.

Method for Manufacturing Diaper 1

Figure 6:
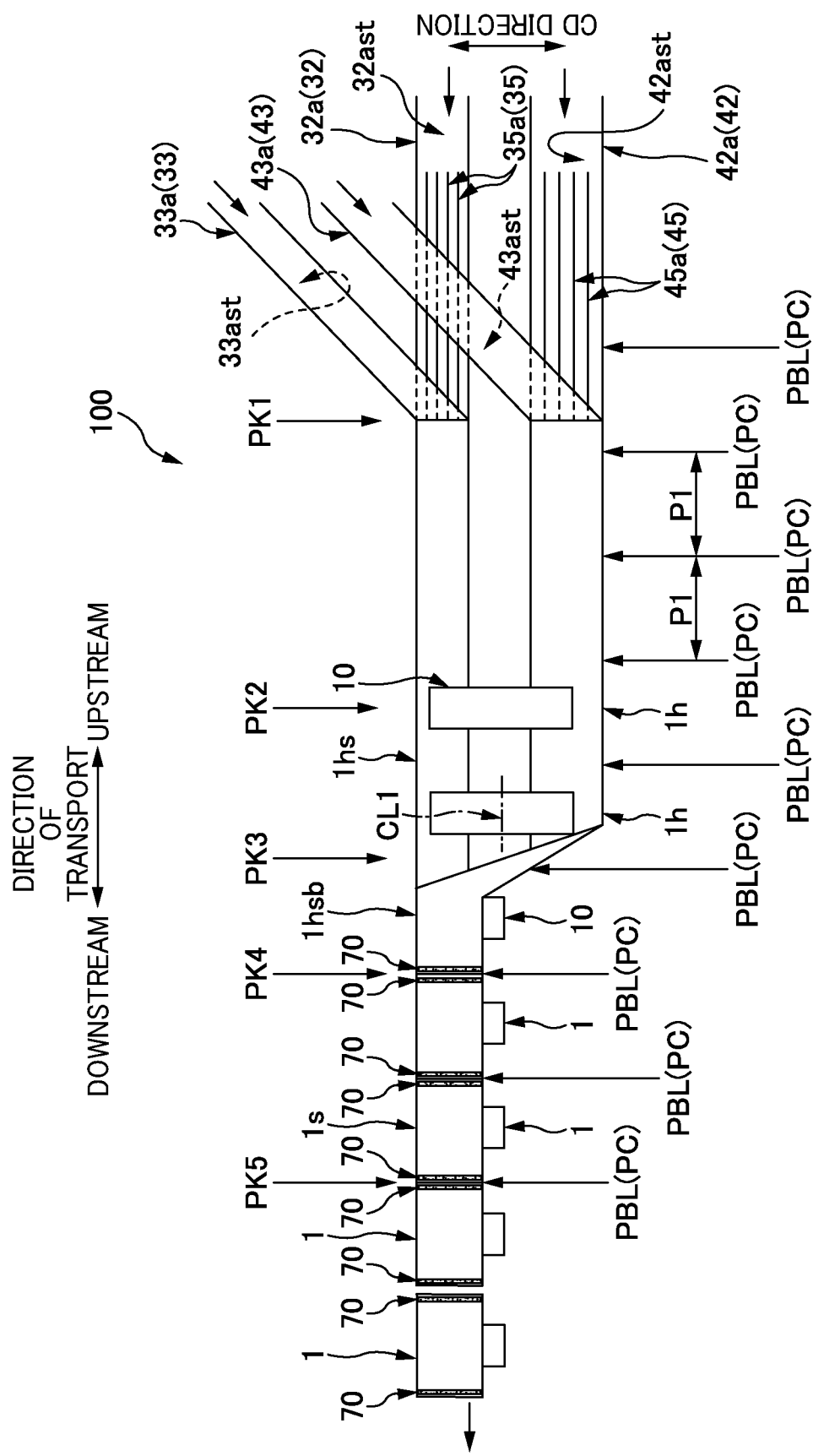
FIG. 6 is a schematic plan view showing a partial perspective view of the manufacturing of the diaper in a production line.

The following describes a method for manufacturing the diaper 1. The diaper 1 is manufactured by a production line 100. FIG. 6 is a schematic plan view showing a partial perspective view of the manufacturing of the diaper 1 in the production line 100.

In the manufacturing line 100, first, two the nonwoven fabric sheets 32 and 33 (sheet-like members) pertaining to the front waist portion 31 are transported in the direction of transport, which correspond to the continuous direction, respectively in the form of the continuous sheets 32a and 33a (sheet-like-member continuous body) that continue in the above-mentioned continuous direction (corresponding to transporting step). Similarly, the two nonwoven fabric sheets 42 and 43 (sheet-like members) pertaining to the back waist portion 41 are also transported in the direction of transport, which corresponds to the continuous direction, respectively in the form of the continuous sheets 42a and 43a (sheet-like-member continuous body) that continue in the continuous direction (transporting step). The sets of two continuous sheets 32a and 33a and two continuous sheets 42a and 43a each pass through a plurality of processing positions PK1 to PK5 that are set in the direction of transport, and are subject to processings that correspond to the processing positions PK1, PK2, and so on.

Note that here, the direction that is orthogonal to both the thickness direction and the direction of transport of the continuous sheets 32a, 33a, 42a, and 43a is defined as a "intersecting direction (that is a direction equivalent to the above-mentioned intersecting direction, and is also referred to as a CD direction)", and in this example, the continuous sheets 32a, 33a, 42a, 43a, (i.e., two continuous sheets 32a and 33a pertaining to the front waist portion 31 and two continuous sheets 42a and 43a pertaining to the back waist portion 41) are transported side-by-side in the CD direction. However, there is no limitation whatsoever to this.

Further, in this example, the above-described processing positions, namely the first to fifth processing positions PK1 to PK5, are set side-by-side in this order from upstream to downstream in the direction of transport. At the processing positions PK1, PK2, and so on, the processes that are performed on the continuous sheet 32a and 33a pertaining to the front waist portion 31 are substantially the same as those performed on the continuous sheet 42a and 43a pertaining to the back waist portion 41.

For this reason, the front waist portion 31 and the back waist portion 41 will not be distinguished from each other when the same content applies hereinafter. For example, in the following description, the term "waist portion 31 (41)" will simply be used, or the term "two continuous sheets 32a and 33a (42a and 43a)" will simply be used. Note that, in such case, in the term indicating the members, such as "the continuous sheets 32a and 33a (42a and 43a)", "the elastic strings 35 (45)", and "the elastic-member continuous bodies 35a (45a)", the reference signs that immediately follow the terms are the reference signs of the members pertaining to the front waist portion 31, and the subsequent reference signs in parentheses are the reference signs of the members pertaining to the back waist portion 41.

As shown in FIG. 6, the two continuous sheets 32a and 33a (42a and 43a) pertaining to the front waist portion 31 (41) are transported in a so-called lateral mode. Specifically, the two continuous sheets 32a and 33a (42a and 43a) are transported such that the direction corresponding to the lateral direction of the diaper 1 conforms to the direction of transport. For this reason, in the two continuous sheet 32a and 33a (42a and 43a), the boundary positions PBL between two diapers 1 that are adjacent in the lateral direction are virtually set at a product pitch P1 in the direction of transport. Also, at the fifth processing position PK5 located at the end of the production line, the boundary position PBL is a cutting target position PC at which the two continuous sheets 32a and 33a (42a and 43a) are cut to produce a single-cut diaper 1.

Note that, in the transporting step, the continuous sheets 32a and 33a (42a and 43a) are transported by an appropriate transporting devices (not shown) such as a belt conveyor or transport rollers. Accordingly, unless otherwise specified, it is assumed that the continuous sheets 32a and 33a (42a and 43a) are transported in the direction of transport by such transporting devices. Examples of the belt conveyor includes a normal belt conveyor that has an endless belt that is driven to rotate as a transporting surface, and a suction belt conveyor that has a function for suction to the outer circumferential surface of an endless belt.

When manufacturing the diaper 1, as shown in FIG. 6, first, the two continuous sheets 32a and 33a (42a, 43a) pertaining to the front waist portion 31 (41) pass the first processing position PK1. While passing, the two continuous sheets 32a and 33a (42a and 43a) are overlaid on each other in the thickness direction. At this time, at the time of overlaying, the elastic-member continuous bodies 35a, 35a, . . . (45a, 45a, . . . ), which continue in the direction of transport, are inserted and arranged side-by-side in the intersecting direction (CD direction) between the two mutually-facing surfaces 32ast and 33ast (42ast and 43ast) of the two continuous sheets 32a and 33a (42a and 43a), in a state of being stretched at a predetermined stretch factor in the direction of transport.

Note that the "stretch factor" of the elastic member 35 (45) is a value R that indicates how many times longer the total length L1 of the elastic member 35 (45) the original total length L0 of the elastic member 35 (45) is (=L1/L0); the total length L0 is a length in a state where in which no force is exerted.

Also, at the same time as or immediately after the overlaying of the two continuous sheets 32a and 33a (42a and 43a) in the thickness direction, the above-mentioned welded portions 50, 50, . . . are formed as joining portions between the two continuous sheets 32a and 33a (42a and 43a), and thus a pair of facing surfaces 32ast and 33ast (42ast and 43ast) of the two continuous sheets 32a and 33a (42a and 43a) are joined (corresponding to joining step).

Here, in the production line 100, the lateral direction of the diaper 1 conforms to the direction of transport, and the vertical direction of the diaper 1 conforms to the intersecting direction (CD direction). For this reason, the welded portions 50 are formed in pairs, on two sides in the intersecting direction of the elastic-member continuous bodies 35a (45a) of the elastic members 35 (45). Specifically, the pair of welded portions 50 and 50 that are side-by-side on respective sides of each continuous body 35a (45a) in the intersecting direction form a welded portion pair 50s. A plurality of such welded portion pairs 50s are formed side-by-side in the direction of transport while spacing between the welded portion pairs 50s that are adjacent in the direction of transport (see FIG. 4, etc.).

Figure 7:
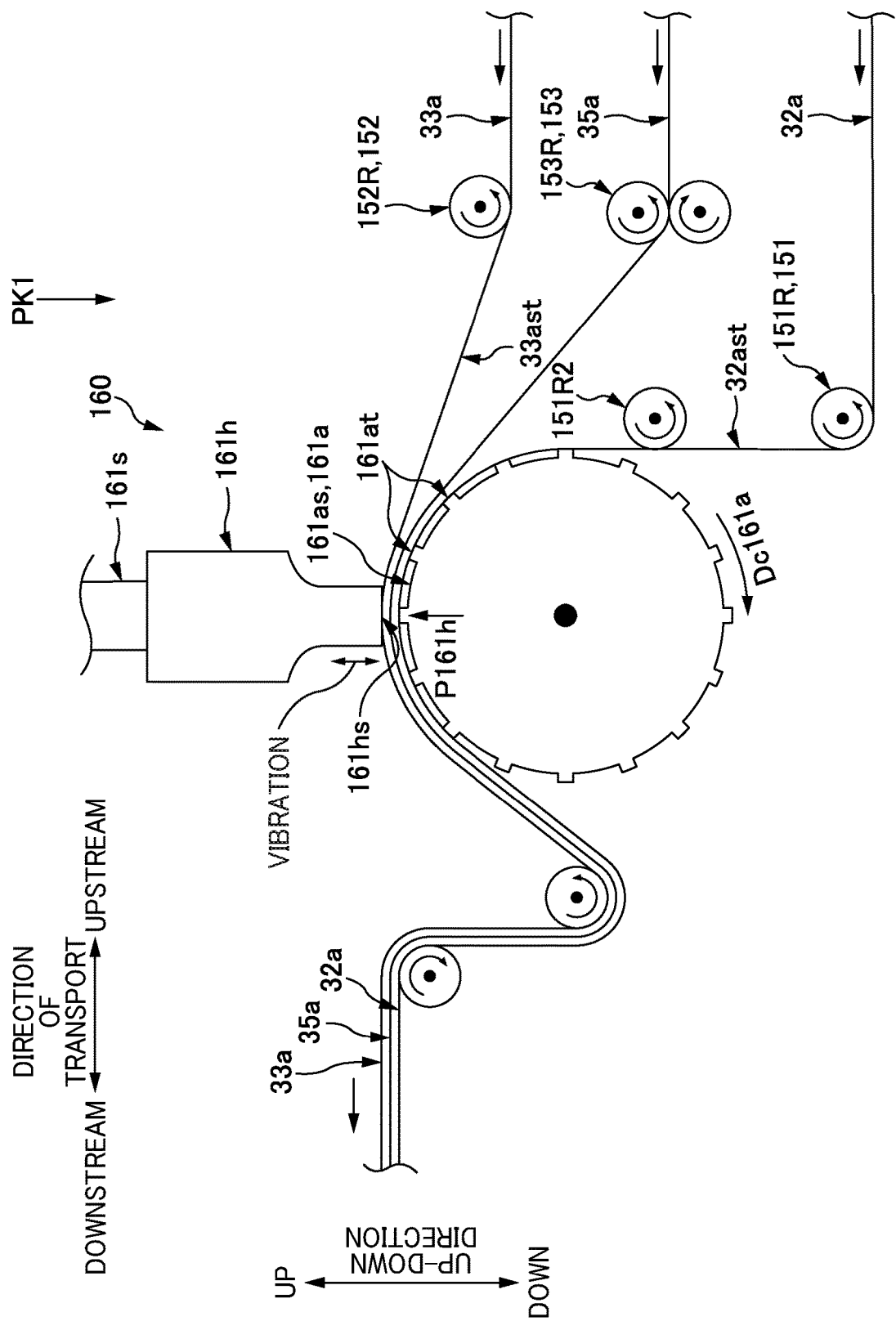
FIG. 7 is a diagram illustrating a processing performed in a joining step at a first processing position.

Such welded portions 50 can be formed using a heat sealing device or an ultrasonic welding device 160 (welded-portion formation device), for example (see FIG. 7). Note that a heat sealing device (not shown) has a pair of rolls that are heated while rotating in the direction of transport, for example. One of the rolls is a heat embossing roll that has protrusion portions corresponding to the welded portions 50 on the outer circumferential surface, and the other roll is an anvil roll that receives the protrusion portions with a smooth outer circumferential surface.

Next, as shown in FIG. 6, the two continuous sheets 32a and 33a pertaining to the front waist portion 31 and the two continuous sheets 42a and 43a pertaining to the back waist portion 41 all pass the second processing position PK2. At the time of the passing, the single-cut absorbent main body 10 produced in a separate step (not shown) is fixed in a state of spanning between the two continuous sheets 32a and 33a pertaining to the front waist portion 31 and the two continuous sheets 42a and 43a pertaining to the back waist portion 41, thus forming the substantially ladder-shaped diaper continuous body 1hs in which substantially H-shaped unfolded diapers 1h, 1h, . . . are continuous with each other.

Next, the approximately ladder-shaped diaper continuous body 1hs passes the third processing position PK3. At the time of the passing, the absorbent main body 10 is folded one time at a predetermined position CL1 of the absorbent main body 10 in the intersecting direction (CD direction), and thereby two continuous sheets 32a and 33a pertaining to the front waist portion 31 and two continuous sheets 42a and 43a pertaining to the back waist portion 41 are overlaid on each other in the thickness direction. The folding can be performed using a fold guiding device (not shown), for example. The fold guiding device has a guide plate and a guide roller that are arranged at predetermined positions in the direction of transport, for example. These guide plates and guide rollers guide the approximately ladder-shaped diaper continuous body 1hs passing at the arrangement position so as to be folded one time.

Next, the diaper continuous body 1hsb in the folded state passes the fourth processing position PK4. At the time of the passing, concerning the two continuous sheets 32a and 33a pertaining to the front waist portion 31 and concerning the two continuous sheets 42a and 43a pertaining to back waist portion 41, the two continuous sheets 32a and 33a and 42a and 43a which are overlaid in the thickness direction are welded at positions on two sides of the cutting target position PC in the direction of transport so as to form a pair of side-joining-portion regions 70, thereby fixing the diaper continuous body 1hsb in the folded state. This consequently produces an underpants-shaped diaper continuous body 1s in which a plurality of underpants-shaped diapers 1, 1, . . . are connected in the lateral direction.

As described in FIG. 7, the side-joining-portion regions 70 have a plurality of side joining portions 71, 71, . . . that are lined up side-by-side in the intersecting direction (CD direction, vertical direction). The side joining portions 71, 71, . . . weld together the continuous sheet 33a of the front waist portion 31 and the continuous sheet 43a of the back waist portion 41, and also weld together the pair of facing surfaces 32ast and 33ast of the continuous sheets 32a and 33a of the front waist portion 31, and also weld together a pair of facing surfaces 42ast and 43ast of the continuous sheets 42a and 43a of the back waist portion 41.

Such side joining portions 70 can be formed using a heat sealing device (not shown), for example. The heat sealing device (not shown) has a pair of rolls that are heated while rotating in the direction of transport, for example. One of the rolls is a heat embossing roll that has protrusion portions corresponding to the shapes of the side joining portions 71 that are formed in the side-joining-portion regions 70, on the outer circumferential surface, and the other roll is an anvil roll that receives the protrusion portions with a smooth outer circumferential surface. Note that, depending on the case, the above-mentioned side joining portions 70 may be formed using a welding device having substantially the same configuration as a later-described ultrasonic welding device 160 in FIG. 7.

Next, as shown in FIG. 6, the underpants-shaped-diaper continuous body 1s passes the fifth processing position PK5. At the time of the passing, the continuous body 1s is cut at the cutting target position PC that is located between a pair of side-joining-portion regions 70, thus obtaining the diaper 1.

Note that, at the time of this cutting, the two continuous sheets 32a and 33a (42a and 43a) pertaining to the front waist portion 31 and the back waist portion 41 and the elastic-member continuous bodies 35a, 35a . . . (45a, 45a . . . ) of the elastic members 35 (45) are cut at the above-mentioned cutting target position. The cutting can be performed using a cutter device (not shown), for example. A cutter device has a pair of rolls that rotates in the direction of transport, for example. One of the rolls is a cutter roll that has a cutter blade provided on the outer circumferential surface, and the other roll is an anvil roll having an outer circumferential surface that receives the cutter blade.

Note that, as described above, the processing at the first processing position PK1 is approximately the same for the members 32a, 33a, 35a pertaining to the front waist portion 31 and for the members 42a, 43a, 45a pertaining to the back waist portion 41. Further, in the following description, of the continuous sheets 32a and 33a of the front waist portion 31, one continuous sheet 32a and the other continuous sheet 33a are also referred to as a "first continuous sheet 32a" and a "second continuous sheet 33a", respectively.

FIG. 7 is a diagram illustrating a processing performed in the joining step at the first processing position PK1. That is, it is a schematic side view of the ultrasonic welding device 160, which is the main equipment for the joining, as seen in the intersecting direction (CD direction).

As shown in FIG. 7, at the first processing position PK1, the followings are arranged at positions located upstream in the direction of transport with respect to the ultrasonic welding device 160: a transport mechanism 151 that transports the first continuous sheet 32a in the direction of transport; a transport mechanism 152 that transports the second continuous sheet 33a in the direction of transport; and a transport mechanism 153 that transports the elastic-member continuous bodies 35a of the elastic members 35 in the direction of transport. Note that, the transport mechanisms 151, 152, and 153 respectively includes: transport rollers 151R, 152R, and 153R that rotate around the rotation axis extending along the intersecting direction; and servo motors (not shown), which are drive sources that drive and rotate the corresponding transport rollers 151R, 152R, and 153R. As a result, the transport roller 151R drives and rotates along the direction of transport to send the first continuous sheet 32a to the ultrasonic welding device 160, and the transport roller 152R also drives and rotates along the direction of transport to send the second continuous sheet 33a to the ultrasonic welding device 160, and the transport roller 153R also drives and rotates along the direction of transport to send the elastic-member continuous bodies 35a of the elastic members 35 to the ultrasonic welding device 160.

On the other hand, the ultrasonic welding device 160 includes: an anvil roll 161a (corresponding to a roll) that rotates along the direction of transport; and a horn 161h that is arranged at a predetermined position P161h in the rotation direction Dc161a of the anvil roll 161a.

The horn 161h is supported by an appropriate support member 161s at the predetermined position P161h so as to be substantially immovable. Further, the horn 161h has a flat vibrating surface 161hs arranged opposite to the outer circumferential surface 161as of the anvil roll 161a. The surface 161hs vibrates in the direction of expanding or reducing the distance from the outer circumferential surface 161as. The frequency of the vibration is, for example, a predetermined value of 20 kHz to 35 kHz, and the amplitude is, for example, a predetermined value of 1 micron to 30 microns. Therefore, the vibrating surface 161hs vibrates ultrasonically, thereby ultrasonically welding both sheets 32a and 33a that are passing between the vibrating surface 161hs and the outer circumferential surface 161as. That is, the above-mentioned welded portions 50 are formed on both sheets 32a and 33a. Incidentally, such vibrations are generated by inputting an electric signal of the above frequency to piezo elements of a converter (not shown) that is connected to the horn 161h.

The anvil roll 161a is rotatably supported around a rotation axis extending along the CD direction, by an appropriate support member (not shown) such as a bearing. The roll 161a is driven and rotated by being given a driving force from a servo motor (not shown), which serves as a driving source. In addition, the followings are wound around the roll 161a on its outer circumferential surface 161as with almost no relative slippage: the first continuous sheet 32a sent from the above-mentioned transport roller 151R; the second continuous sheet 33a sent from the above-mentioned transport roller 152R; and the elastic-member continuous bodies 35a of the elastic members 35 sent from the above-mentioned transport roller 153R. Therefore, by driving and rotating the anvil roll 161a, the first continuous sheet 32a, the second continuous sheet 33a, and the elastic-member continuous bodies 35a of the elastic members 35 are transported along the outer circumferential surface 161as of the roll 161a at the same transport speed value as the circumferential speed value of the anvil roll 161a. In other words, both continuous sheets 32a and 33a and the elastic-member continuous bodies 35a of the elastic members 35 are transported in the transport path that curves along the outer circumferential surface 161as.

Here, the circumferential speed value (mpm) of the above-mentioned transport roller 151R of the first continuous sheet 32a and the circumferential speed value (mpm) of the above-mentioned transport roller 152R of the second continuous sheet 33a are approximately the same as the circumferential speed value (mpm) of the anvil roll 161a. Therefore, the first continuous sheet 32a and the second continuous sheet 33a are wrapped around the anvil roll 161a in a state where these sheets are not stretched but tightened to the extent that they do not loosen. On the other hand, the circumferential speed value (mpm) of the transport roller 153R of the elastic-member continuous bodies 35a (45a) of the elastic members 35 (45) is approximately 1/stretch factor times the circumferential speed value (mpm) of the anvil roll 161a. Therefore, while passing between the transport roller 153R and the anvil roll 161a, the elastic-member continuous bodies 35a (45a) of the elastic members 35 (45) are stretched to the above-described stretch factor and wraps around the anvil roll 161a in the stretched state.

Further, in this example, regarding the order of wrapping around the anvil roll 161a, first, the first continuous sheet 32a is wrapped, and next the elastic-member continuous bodies 35a of the elastic members 35 are wrapped, and finally the second continuous sheet 33a is wrapped. As a result, these are brought into a state where the elastic-member continuous bodies 35a of the elastic members 35 are interposed between the first continuous sheet 32a and the second continuous sheet 33a, on the outer circumferential surface 61as of the anvil roll 161a.

Furthermore, as shown in FIG. 7, on the outer circumferential surface 161as of the anvil roll 161a, a plurality of protrusion portions 161at, 161at, . . . are formed in a protruding manner, corresponding to the aforementioned welded portions 50. When the first and second continuous sheets 32a and 33a between which the elastic-member continuous bodies 35a of the elastic members 35 are interposed pass the arrangement position P161h of the horn 161h because of the rotation of the anvil roll 161a, ultrasonic wave vibration energy is generated from the vibrating surface 161hs of the horn 161h so as to be applied to both sheets 32a and 33a. Therefore, the pair of facing surfaces 32ast and 33ast of the sheets 32a and 33a partially generate heat and melt at the positions corresponding to the protrusion portions 161at, and as a result, the plurality of welded portions 50 as mentioned above make the pair of facing surfaces 32*ast* and 33*ast* be joined together in a discontinuously dispersed joining pattern. Then, first continuous sheet 32*a* and second continuous sheet 33*a* joined by the welded portions 50 are transported to the aforementioned second processing position PK2 located downstream in the direction of transport, in a state where the elastic-member continuous bodies 35*a* of the elastic members 35 are interposed therebetween.

Also, it is recommended that the circumference (length in the circumferential direction) of the outer circumferential surface 161*as* of the anvil roll 161*a* is made to be the length of one piece or multiple pieces (multiple of one piece) of the underpants-shaped diaper 1 in the direction of transport. For example, n patterns (n=1, 2, 3 . . . ) of the welded portions 50 shown in FIG. 4 are formed along the rotation direction of the outer circumferential surface 161*as* of the anvil roll 161*a*. And, in the direction of transport (lateral direction of the diaper 1), the welded portions 50 are formed synchronously so that each welded portion row 60 is formed without shifting its position. In this way, each of the welded portions 50 (welded portion row 60) can be arranged without timing deviation. Furthermore, if the timing is deviated, the fact is easy to judge visually because one welded portion row 60 overlaps the side-joining-portion region 70, for example. This makes it possible to accurately judge the quality of the product.

Stretchability of Waist Portion 20

The waist portion 20 (the stretchable sheet consisting of the front waist portion 31 and the back waist portion 41) of the diaper 1 formed in this way exhibits the stretchability in the lateral direction due to the elastic members 35 (45) attached to the waist portion 20. Then, the elastic members 35 (45) are sandwiched in the intersecting direction (vertical direction) between a pair of the welded portion pairs 50*s* constituted by the welded portions 50 that joins the first sheet 32 (42) and the second sheet 33 (43) to each other, and thereby being attached to the waist portion 20 (stretchable sheet).

There has conventionally been cases where the stretchable sheet to which the elastic members (e.g., elastic strings) are attached by the welded portion pairs deteriorates in stretchability during usage. For example, elastic members such as elastic strings change in thickness (outer diameter) when being stretched and when being contracted, and therefore, when the outer diameter of an elastic member becomes thinner during stretching, there are cases where the elastic member comes out of between the welded portion pair. In such a case, there is a risk that the displacement of the elastic members partially arise in the continuous direction, making the stretchability uneven, and causing the stretchability to deteriorate throughout the stretchable sheet. In addition, if an elastic string (elastic member) is cut off at any position in the lateral direction, there is a risk that the elastic string comes out of between the welded portion pair when contracting from the cutting point, resulting in so-called rubber coming off.

In contrast, in the stretchable sheet of one or more embodiments, a part of the surface is made damaged when attaching an elastic member 35 (45), thereby prevents the elastic member 35 (45) from coming off from the welded portion pair 50*s*. A specific method for attaching the elastic members 35 (45) will be described below.

Figure 8:
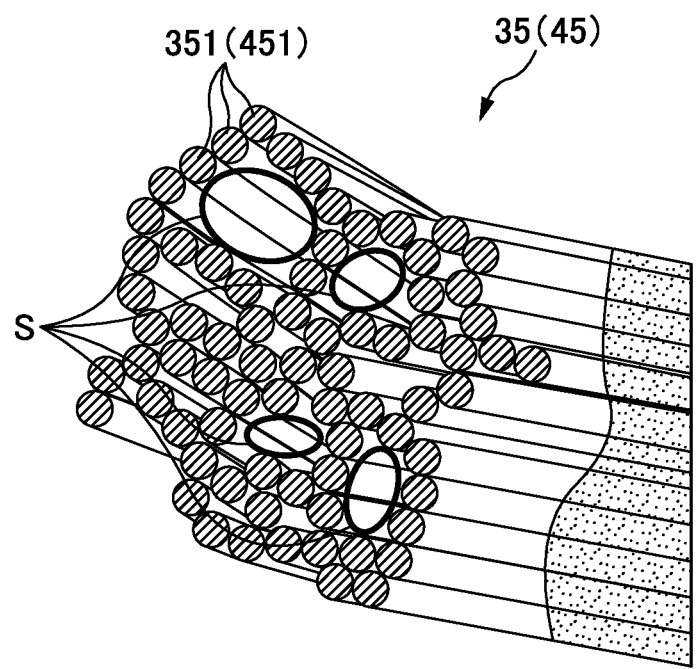
FIG. 8 is a diagram illustrating the structure of an elastic member.
Figure 9:
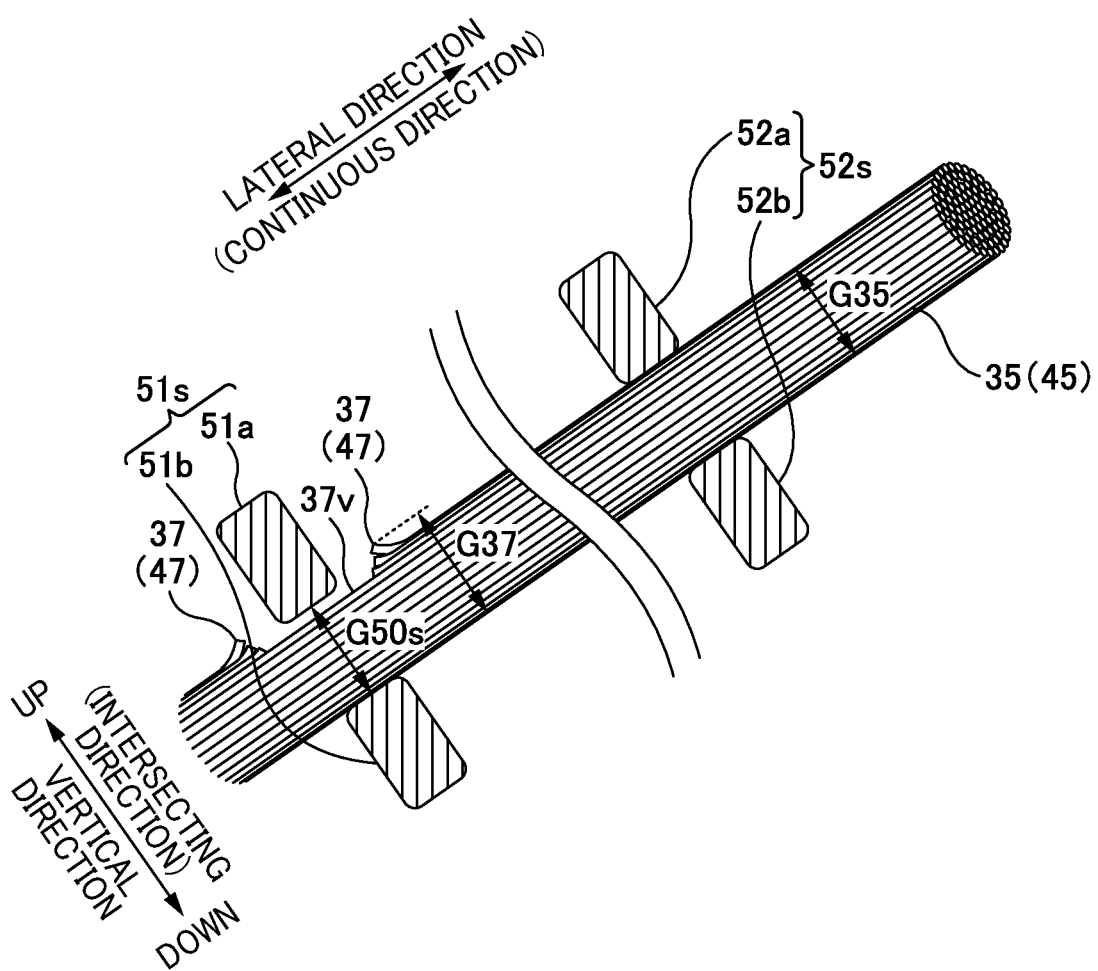
FIG. 9 is a schematic enlarged view showing how the elastic member is attached.

FIG. 8 is a diagram illustrating the structure of the elastic member 35 (45). FIG. 9 is a schematic enlarged view showing how the elastic member 35 (45) is attached. FIG. 9 shows a state in which the elastic member 35 (45) is stretched in the continuous direction by a predetermined stretch factor.

Examples of the elastic members 35 (45) used in one or more embodiments include polyurethane, polyester, and latex (natural rubber). Among these, as shown in FIG. 8, string-like elastic members in which a plurality of elastic fibers 351 (451) (elastic threads) made from polyurethane, polyester, or the like are aggregated may be used. In this case, the outer shape of the elastic member 35 (45) becomes uneven, the surface area where the waist elastic member 35 (45) is in contact with constituent fibers of a sheet increases, and this increases its frictional force with the sheet. This can make it likely to suppress the coming off of the elastic member 35 (45) from the side-joining-portion region 70 and from between the welded portion pair 50*s*.

Further, in each of the elastic members 35 (45), gaps S may be formed among the elastic fibers 351 (451). By doing so, when forming the side joining portions 71, even if a waist elastic member 35 (45) is compressed by the protrusion portions of the above-mentioned heat embossing roll or the like, the gaps S are compressed and an escape margin is created, and this makes the elastic member 35 (45) less likely to be cut. Further, when compressing the gap S, the position of the elastic member 35 (45) is more likely to shift in the vertical direction of the diaper 1, and this makes it possible to suppress that the elastic member 35 (45) is cut off by being compressed by the protrusion portions.

In the manufacturing process of the diaper 1, when attaching such an elastic member 35 (45) to the front waist portion 31 (41), a plurality of the welded portion pairs 50*s* are formed by ultrasonic welding (joining step mentioned above) with the ultrasonic welding device 160 as illustrated in FIG. 7, making the elastic member 35 (45) sandwiched between these welded portion pairs 50*s* in the intersecting direction and held. At that time, in one or more embodiments, a part of the surface of the elastic member 35 (45) is subject to ultrasonic vibration by bringing it into contact with the horn 161*h* of the ultrasonic welding device 160, thereby forming a damaged portion 37 where the elastic fiber 351 (451) is partially damaged.

In FIG. 9, as two welded portion pairs adjacent to each other in the continuous direction (lateral direction), there are arranged a first welded portion pair 51*s* and a second welded portion pair 52*s*. Among these, the upper welded portion 51*a* of the first welded portion pair 51*s* comes into contact with an elastic member 35 (45), and thereby the contact portion is damaged, forming the damaged portion 37 (47). That is, among the plurality of the elastic fibers 351 (451) (elastic thread) constituting the elastic member 35 (45), several of the elastic fibers 351 (451) are cut at the locations in the continuous direction where the fibers contacts the upper welded portion 51*a*. The cut elastic fibers 351 (451) expands in the intersecting direction (vertical direction) while contracting from the cutting locations to both sides in the continuous direction (lateral direction). Therefore, in the damaged portion 37, the outer diameter of the elastic member 35 (45) is thicker than the remaining portions (portions where the damaged portion 37 is not formed).

For example, as shown in FIG. 9, letting the gap between the upper welded portion 51*a* (52*a*) and the lower welded portion 51*b* (52*b*) of the first welded portion pair 51*s* (52*s*) be G50*s*, the elastic member 35 (45) is arranged in a state where it is stretched so that its outer diameter G35 is smaller than the gap G50*s* (G50*s*>G35). On the other hand, in the damaged portion 37 of the elastic member 35 (45), a part of the elastic fiber 351 (451) contracts and thereby the elastic member 35 (45) expands in the intersecting direction. Consequently, the outer diameter G37 of the elastic member 35 in the damaged portion 37 becomes larger than the gap G50s (G37>G50s).

The damaged portion 37 is provided between the first welded portion pair 51s and the second welded portion pair 52s in the continuous direction. Therefore, if the damaged portion 37 (47) gets caught in either of the first welded portion pair 51s and the second welded portion pair 52s, the movement of the elastic member 35 (45) along the continuous direction is obstructed, making it the elastic member 35 (45) less likely to come off from the welded portion pair 50s. That is, the elastic member 35 (45) is less likely to relatively move with respect to the welded portion pairs 50s in the continuous direction, suppressing the displacement of the elastic member 35 (45) in the continuous direction, rubber coming off and the like. As a result, the elastic member 35 (45) is firmly attached to the first sheet 32 (42) and the second sheet 33 (43) that constitute the front waist portion 31 (41), and the stretchability of the front waist portion 31 (41) (stretchable sheet) is made less likely to deteriorate.

In addition, in the elastic member 35 (45), as shown in FIG. 9, the elastic fibers 351, which are cut off by the upper welded portion, contract from the cutting point (upper welded portion 51a) to both sides in the continuous direction, forming the damaged portions 37 and 37. A groove-shaped portion 37v is formed in a region between the damaged portions 37 and 37. By fitting the upper welded portion 51a into this groove-shaped portion 37v, it can make the displacement of the elastic member 35 (45) in the continuous direction less likely to occur.

In one or more embodiments, the welded portions 50 are formed by ultrasonic joining. Therefore, the position and shape of the welded portion pair 50s are formed accurately, and it is likely to ensure sufficient strength of the welded portion pair 50s, making it possible to effectively suppress the displacement of the elastic members 35 (45) is It in the continuous direction, rubber coming off, and the like.

As mentioned above, in the joining step when manufacturing the diapers 1, when being in a state where the elastic member 35 (45) stretches, the outer diameter G37 of the elastic member 35 (45) in the damaged portion 37 is larger than the gap G50s between the upper welded portion 50a and the lower welded portion 50b. Therefore, even if the front waist portion 31 (41) is in the stretched state, the elastic member 35 (45) is less likely to come off from the welded portion pair 50s, making it possible to maintain good stretchability. Furthermore, when the elastic member 35 (45) contracts during usage of the diaper 1, etc., the outer diameter G37 becomes further thicker, and this makes the damaged portion 37 (47) more likely to be caught in the welded portion pair 50s, making the elastic member 35 (45) less likely to come off. Therefore, in one or more embodiments, it is likely to maintain a good stretchability regardless of whether the front waist portion 31 (41) (stretchable sheet) contracts or stretches.

In addition, since the elastic member 35 (45) is composed of an aggregation of the plurality of elastic fibers 351 (451) (elastic thread), when forming the damaged portion 37 (47), it is likely to suppress the elastic member 35 (45) from being cut as a whole. If the elastic member 35 (45) is composed of a single thick elastic fiber, there is a risk that, when a notch (damaged portion) has been formed on the surface of the elastic fiber, the notch spreads in the radial direction of the elastic fiber, causing the breakage of the entire fiber. In contrast, in one or more embodiments, even if some of the elastic fibers 351 (451) are severed at the damaged portion 37 (47), the effect is less likely to affect the other elastic fibers 351 (451). That is, it is unlikely that all the elastic fibers 351 (451) that constitute the elastic member 35 (45) are severed. Therefore, it is likely to prevent the elastic member 35 (45) from being severed as a whole, and it is possible to make the stretchability less likely to deteriorate.

Note that a plurality of the elastic fibers 351 (451) may be damaged in the damaged portion 37 (47) of the elastic member 35 (45). That is, two or more the elastic fibers 351 (451) may be severed. As described above, in the damaged portion 37, damaged (cut) elastic fiber 351 (451) contracts, thereby increasing the outer diameter G37 of the damaged portion 37. Therefore, as the damaged (cut) elastic fibers 351 (451) increase, the outer diameter G37 is more likely to be thicker, and the elastic member is more likely to get caught by the welded portion pair 50s. In other words, compared to the case where only one the elastic fiber 351 (451) is damaged, in the case where two or more elastic fibers 351 (451) are damaged, the elastic member 35 (45) is less likely to come off from the welded portion pair 50s, enabling to make the stretchability less likely to deteriorate.

However, with respect to the continuous direction, in the portion of the elastic member 35 (45) where the damaged portion 37 (47) is formed, the number of damaged elastic fibers 351 (451) may be smaller than the number of undamaged elastic fibers 351 (451). In the portion where the damaged portion 37 (47) is formed, as the damaged (cut) elastic fibers 351 (451) increase, the strength of the elastic member 35 (45) becomes weaker, causing a risk that the entirety of the elastic member 35 (45) is more likely to be severed. In contrast, in one or more embodiments, as shown in FIG. 9, in the portion where the damaged portion 37 (47) is formed, only two to three elastic fibers 351 (451) are damaged (cut), and most other elastic fibers 351 (451) are not damaged. Therefore, it is likely to prevent the elastic member 35 (45) from being severed as a whole, making the stretchability less likely to deteriorate.

Further, in the damaged portion 37 (47), the damaged elastic fibers 351 (451) may have a portion that is peeled off from the undamaged elastic fibers 351 (451). If a damaged elastic fiber 351 (451) and an undamaged elastic fiber 351 (451) are joined to each other, the damaged elastic fiber 351 (451) is less likely to contract in the continuous direction. In this case, the outer diameter G37 of the damaged portion 37 (47) is less likely to increase, and the elastic member 35 (45) does not get caught by the welded portion pair 50s, causing a risk of the displacement of the elastic member 35 (45) in the continuous direction and rubber coming off. In contrast, if the damaged elastic fiber 351 (451) is peeled off from the undamaged elastic fiber 351 (451), the damaged elastic fiber 351 (451) contracts on its own and the outer diameter G37 is likely to be thicker, making it likely to get caught by the welded portion pair 50s. Note that, as the number of the elastic fibers 351 (451) that are peeled off in the damaged portion 37 (47) increases, the outer diameter G37 is likely to become thicker, and it can make the stretchability further less likely to deteriorate.

Further, the elastic member 35 (45) may be twisted in the continuous direction. That is, a plurality of the elastic fibers 351 (451) that constitute the elastic member 35 (45) may be twisted together in the continuous direction. With such a configuration, fibers of the nonwoven fabric which constitutes the first sheet 32 (42) and the second sheet 33 (43) get entangled or caught in the "twisted" portions of the elastic member 35 (45), and as a result the frictional force between the elastic member 35 (45) and the nonwoven fabric is more likely to increase. Therefore, it prevents the displacement of the elastic member 35 (45) in the continuous direction, rubber coming off, and the like, making the stretchability less likely to deteriorate.

In addition, in the case of defining a third welded portion pair 53s and a fourth welded portion pair 54s (both not shown) which are different from the first welded portion pair 51s and the second welded portion pair 52s and which are adjacent to each other in the continuous direction, the damaged portion 37 (47) may not be provided between the third welded portion pair 53s and the fourth welded portion 54s in the continuous direction. In other words, among pairs of welded portion pairs 50s and 50s that are located adjacent in the continuous direction, some may be ones having the damaged portion 37 (47), and the others may be ones not having the damaged portion 37 (47). In the case where the damaged portion 37 (47) is provided between all pairs of the welded portion pairs 50s and 50s that are located adjacent in the continuous direction, there is a high probability that the elastic member 35 (45) is severed somewhere. In contrast, if the damaged portion 37 (47) is not provided between a pair of the welded portion pairs 50s and 50s that are located adjacent in the continuous direction, the elastic member 35 (45) is made less likely to be cut between the pair of the welded portion pairs 50s and 50s. This makes it possible to decrease the probability of the elastic member 35 (45) being cut, compared to the above-mentioned case. This makes it likely to suppress the stretchability from deteriorating.

In the front waist portion 31 (41) (stretchable sheet) of one or more embodiments, the number of the welded portion pairs 50s that are located between the one-side end and other-side end of the elastic member 35 (45) in the lateral direction (continuous direction) is greater than the number of the damaged portions 37 (47) provided between the same one-side end and other-side end. In other words, for each of the elastic members 35 (45), among locations between pairs of the welded portion pairs 50s and 50s that are located adjacent in the continuous direction, some are ones where the damaged portion 37 (47) is present and the others are ones where the damaged portion 37 (47) is not present. Therefore, for each of the elastic members 35 (45), the displacement in the continuous direction and rubber coming off are suppressed, and the elastic member 35 (45) is less likely to be cut. This makes the front waist portion 31 (41) (stretchable sheet) as a whole possible for the stretchability to be less likely to deteriorate.

In addition, the damaged portion 37 (47) of the elastic member 35 (45) may not have a portion exposed outside the first sheet 32 (42) and the second sheet 33 (43) in the thickness direction, the first sheet 32 (42) and the second sheet 33 (43) being located on both sides of the elastic member 35 (45) in the thickness direction. In other words, the damaged portion 37 (47) may not penetrate the first sheet 32 (42) and the second sheet 33 (43) in the thickness direction. In the case where the damaged portion 37 (47) is exposed outside the first sheet 32 (42) in the thickness direction (i.e. on the non-skin side), the cutting point of the elastic member 35 (45) is more likely to be visible from outside of the diaper 1. This causes a risk that the user is more likely to be reminded of the feeling of anxiety on deterioration in quality. On the other hand, in the case where the damaged portion 37 (47) is exposed outside the second sheet 33 (43) in the thickness direction (i.e. on the skin side), the damaged portion 37 (47) comes into contact with the wearer's skin, and this makes the texture deteriorate, causing a risk of making the wearer feel discomfort. In contrast, in the case where the damaged portion 37 (47) is not exposed outside the first sheet 32 (42) and the second sheet 33 (43) in the thickness direction, it is possible to suppress for the user to feel anxiety or discomfort.

Further, as shown in FIGS. 2 and 4, when the diaper 1 is viewed in the front-back direction, at least a portion of the elastic member 35 (45) is located overlapping with the side-joining-portion region 70. In the side-joining-portion region 70, the front waist portion 31 and the back waist portion 41 are attached in the thickness direction in a compressed manner at the side joining portions 71, and the first sheet 32 (42) and the second sheet 33 (43), which constitute each of the waist portions 31 and 41, are also attached in the thickness direction in a compressed manner. Therefore, in the case where the elastic member 35 (45) is located overlapping with the side-joining-portion region 70, the elastic member 35 (45) is likely to be fixed in the state of being sandwiched between the first sheet 32 (42) and the second sheet 33 (43) in the thickness direction. As a result, in the lateral end (side-joining-portion region 70), rubber coming off as described above is less likely to occur, and during usage of the diaper 1, it is possible to prevent the stretchability of the front waist portion 31 (41) from deteriorating to cause the deterioration of the fit.

In addition, as shown in FIG. 5, in the front waist portion 31 (41) of the diaper 1, a plurality of the side joining portions 71 are arranged in the side-joining-portion region 70 at intervals in the vertical direction, but the width W71 of the side joining portion 71 in the lateral direction may be larger than the width W50 of the welded portion 50 in the lateral direction (W71>W50). As shown in FIG. 4, the welded portions 50 are dispersed throughout the front waist portion 31, and therefore if the area (width) of the welded portions 50 is large, this makes texture around the waist hard during usage of the diaper 1, causing a risk of making the wearer likely to feel discomfort. Therefore, in one or more embodiments, the width W50 of the welded portions 50 is made smaller than the width W71 of the side joining portion 71. As a result, compared to the opposite case, it is possible to make the wearer less likely to feel unpleasantness and discomfort.

Figure 10:
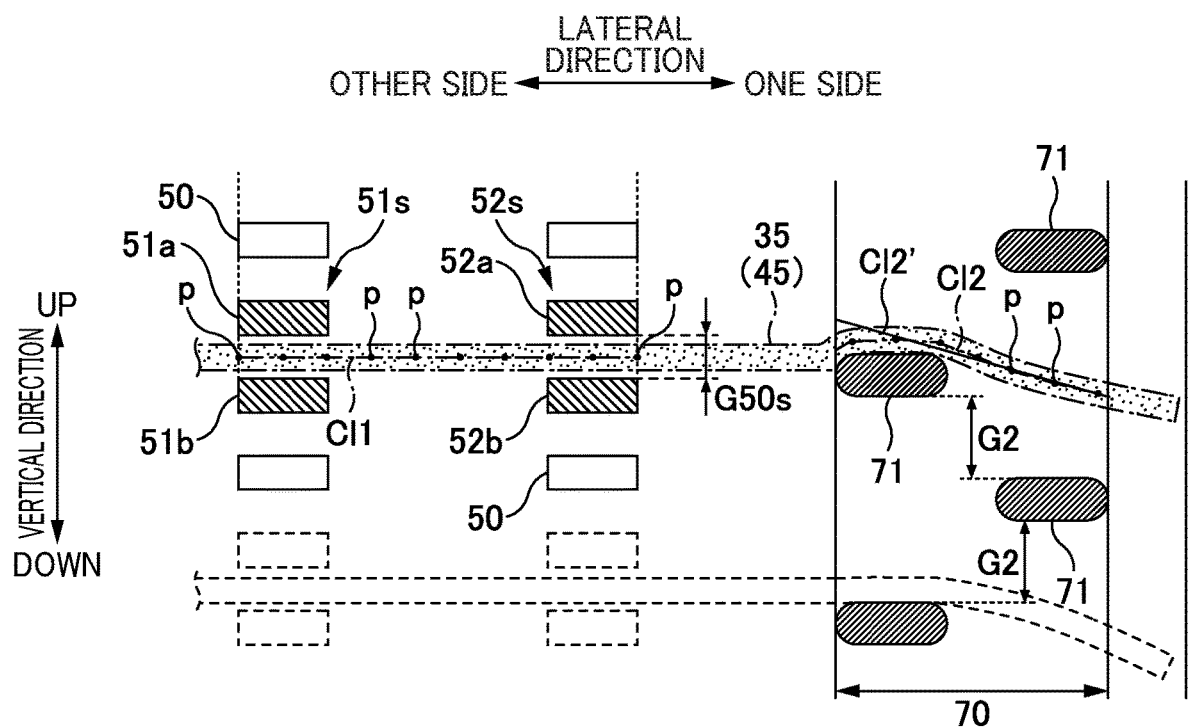
FIG. 10 is a diagram illustrating a state in which ends of waist elastic members are in contact with side joining portions.

FIG. 10 is a diagram illustrating a state in which ends of the waist elastic members 35 (45) are in contact with the side joining portions 71, and is an enlarged view of the region corresponding to FIG. 5. When the diaper 1 (waist portion 20) in the stretched state is viewed in the front-back direction (thickness direction), the center line Cl2 of a portion of the elastic member 35 (45) that is located in the side-joining-portion region 70 located on the one side (or the other side) in the lateral direction, is inclined with respect to the center line Cl1 of a portion of the same elastic member 35 (45) that is located between the first welded portion pair 51s and the second welded portion pair 52s.

The center lines Cl1 and Cl2 of the elastic member 35 (45) are center lines that divide the elastic member 35 (45) in the vertical direction. In addition, the portion of the elastic member 35 (45) that is located between the first welded portion pair 51s and the second welded portion pair 52s is a portion of the elastic member 35 (45) that is located between the lateral outermost end of the first welded portion pair 51s and the lateral innermost end of the second welded portion pair 52s.

The portion of the elastic member 35 (45) that is located between the first welded portion pair 51s and the second welded portion pair 52s is arranged extending along the lateral direction and exhibits the stretchability in the lateral direction. Therefore, the center line Cl1 substantially conforms to the line extending along the lateral direction. On the other hand, in the side-joining-portion region 70, the end of the elastic member 35 (45) that has been cut off during the manufacture of the diaper 1 is sandwiched and fixed between the first sheet 32 (42) and the second sheet 33 (43), and the stretchability does not exhibit. Therefore, the center line Cl2 can be inclined with respect to the center line Cl1 (with respect to the lateral direction).

Further, the location of the elastic member 35 (45) in the side-joining-portion region 70 is not restricted by the welded portion pair 50s. Therefore, even in a state where the waist portion 20 is stretched, the probability that the center line Cl2 has a curved shape as shown in FIG. 10 is high. Therefore, if it has been visually conformed the center lined that at least a part of the center line Cl2 is inclined with respect to the center line Cl1 (lateral direction), the center line Cl2 is inclined with respect to the center line Cl1.

More rigorous confirmation methods include the following methods. First, an enlarged image of the waist portion 20 in the stretched state is taken using a digital microscope or the like. On the captured image data, the center points p of the target elastic member 35 (45) in the vertical direction is specified at predetermined intervals in the lateral direction. A straight line connecting the specified plurality of center points p or a straight line approximated by the method of least squares is obtained as the center lines Cl1 and Cl2', and the slopes thereof are compared. In addition, when confirming the slopes of the center lines Cl1 and Cl2, the confirmation may be made in a state where, by releasing the joining of the side-joining-portion region 70, the diaper 1 is opened and unfolded flat (see FIG. 2), or in a state where the front waist portion 31 and the back waist portion 41 are connected.

The direction to which the center line Cl1 of the elastic member 35 (45) located between the first welded portion pair 51s and the second welded portion pair 52s conforms (lateral direction) is the direction in which the contractive force of the elastic member 35 (45) acts. In other words, this is the direction in which a force that causes the elastic member 35 (45) to come off from the side-joining-portion region 70 (rubber coming off) acts. Therefore, by inclining the center line Cl2 of the elastic member 35 (45) in the side-joining-portion region 70 with respect to the center line Cl1 (lateral direction), it is possible to prevent a force that causes rubber coming off from directly acting on a portion of the elastic member 35 (45) that is located in the side-joining-portion region 70 (it is possible to disperse a force that causes rubber coming off). Therefore, it is possible to suppress the coming off of the elastic member 35 (45) from the side-joining-portion region 70.

Also, in order to make the elastic member 35 (45) be inclined in the side-joining-portion region 70, a part of the elastic member 35 (45) may be in contact with the side joining portion 71 in the side-joining-portion region 70 on the one side (or the other side) in the lateral direction (see FIG. 10). By doing so, the elastic member 35 (45) conforms to the outline of the side joining portion 71, and this can make the center line Cl2 of the elastic member 35 (45) located in the side-joining-portion region 70 be inclined with respect to the center line Cl1 (lateral direction). In this case, since the frictional force occurs at the location where the elastic member 35 (45) and the side joining portion 71 come into contact, it is possible to further suppress the coming off of the elastic member 35 (45) from the side-joining-portion region 70.

Figure 11:
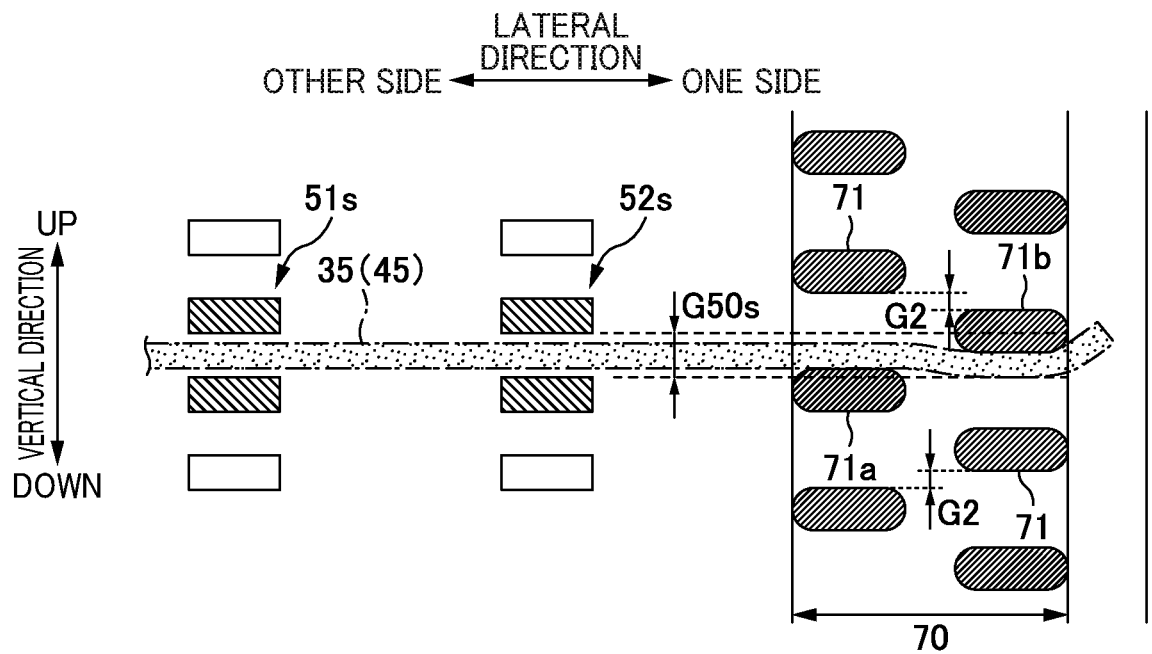
FIG. 11 is a diagram illustrating a state in which the elastic member is sandwiched between the side joining portions in the vertical direction.

Further, the side-joining-portion region 70 may be modified as follows. FIG. 11 is a diagram showing a modified example of the side-joining-portion region 70 and a state in which the elastic member 35 (45) is sandwiched between the side joining portions 71 in the vertical direction. In FIG. 11, the side joining portion 71 is arranged so that the distance G2 in the vertical direction between a first side joining portion 71a and a second side joining portion 71b that are located adjacent in the vertical direction with interposing the elastic member 35 (45) in between is shorter than the distance G50s in the vertical direction between the welded portion pair 50s.

In this case, a plurality of the side joining portions 71 (partially) are likely to be arranged between the welded portion pair 50s, that is, in a region that the space where the elastic member 35 (45) passes overlap with respect to the vertical direction. Therefore, a part of the elastic member 35 (45) is likely to be sandwiched in the vertical direction (intersecting direction) between the side joining portion 71 (in FIG. 11, the first side joining portion 71a and the second side joining portion 71b). This increases the frictional force between the elastic member 35 (45) and the pair of upper and lower side joining portions 71 (the first side joining portion 71a and the second side joining portion 71b). Therefore, the elastic member 35 (45) is prevented from coming off from the side-joining-portion region 70, and the stretchability of the waist portion 20 is less likely to deteriorate. In addition, in the side-joining-portion region 70, when the elastic member 35 (45) contracts in the lateral direction (continuous direction), the outer diameter of the elastic member 35 becomes thicker and the frictional force with the side joining portion 71 becomes larger. Accordingly, rubber coming off and the like becomes less likely to occur.

Figure 12A:
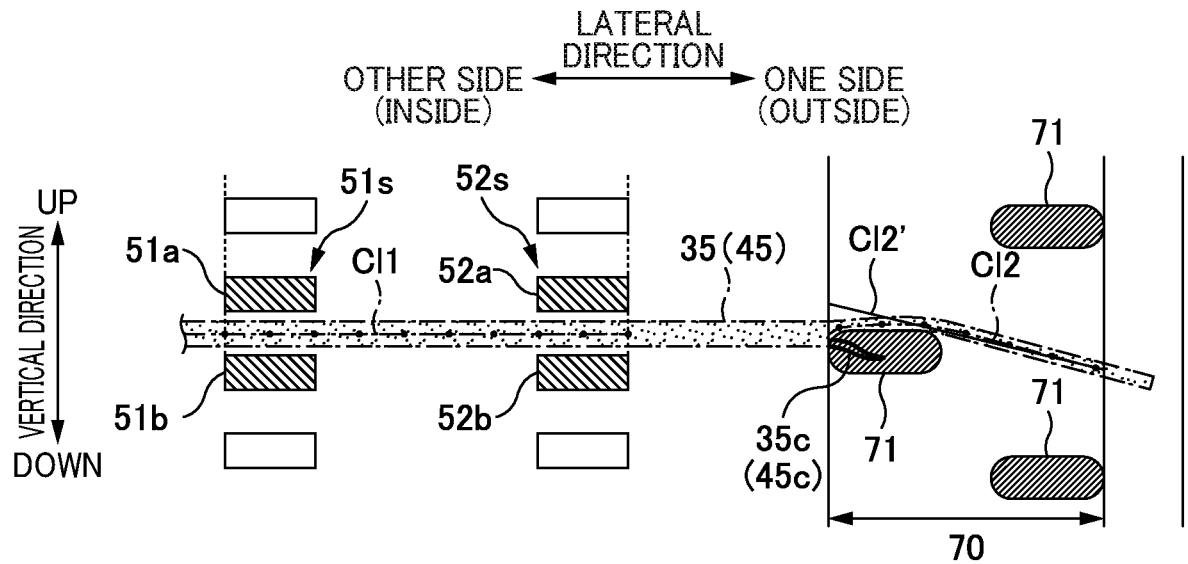
FIG. 12A is a diagram illustrating a state in which the side joining portion and the elastic member overlap in at least a partial region.
Figure 12B:
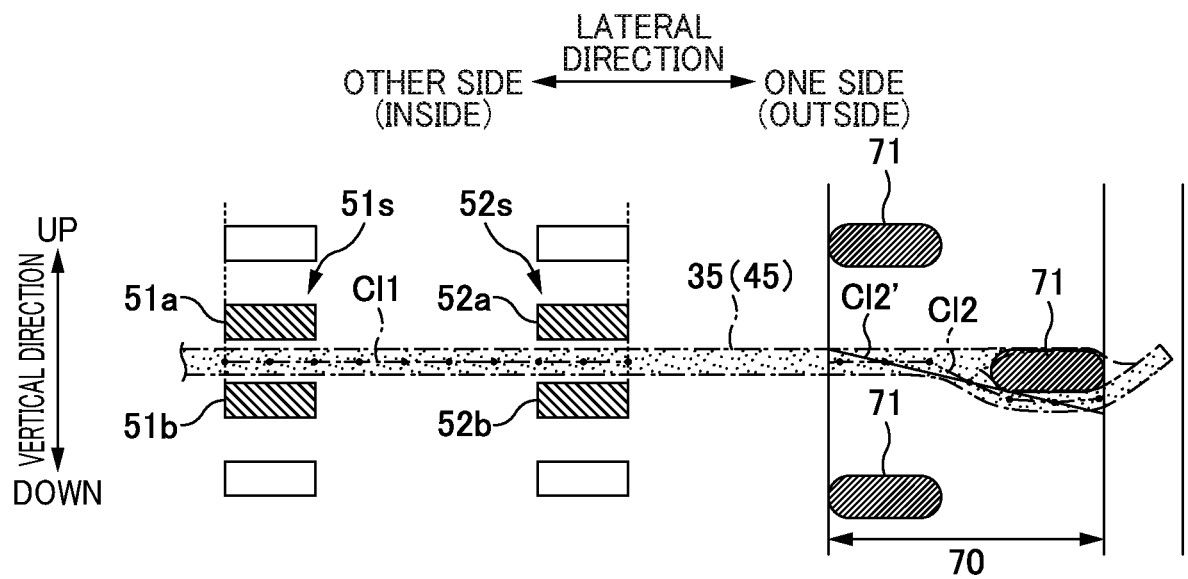
FIG. 12B is a diagram illustrating a state in which the side joining portion and the elastic member overlap in at least a partial region.

FIGS. 12A and 12B are diagrams showing another modified example of the side-joining-portion region 70, and a state in which the side joining portion 71 and the elastic member 35 (45) overlap in at least a partial region. In the state shown in FIGS. 12A and 12B, a part of the elastic member 35 (45) is sandwiched between the first sheet 32 (42) and the second sheet 33 (43) due to the side joining portion 71.

In this case, in the side joining portion 71, a part of the elastic member 35 (45) is strongly sandwiched between the sheets, so that the coming off of the elastic member 35 (45) from the side-joining-portion region 70 can be further suppressed. In addition, as shown in FIG. 12A, even if a part of the elastic member 35 (45) is cut off in the middle in the lateral direction, it is sufficient that the cut end portion 35c (45c) is fixed at the side joining portion 71. In this case as well, the coming off of the elastic member 35 (45) from the side-joining-portion region 70 is suppressed, and the stretchability of the waist portion 20 is less likely to deteriorate.

Further, the waist portion 20 of the diaper 1 may have a portion where a part of each of the elastic members 35 (45) is discontinuous in the lateral direction. In one or more embodiments, as shown in FIG. 2, the elastic members 35 (45) are cut in a part of the region where the front waist portion 31 (41) and the absorbent main body 10 overlap when viewed in the thickness direction. And thereby the elastic members 35 (45) are discontinuous in the lateral direction (continuous direction), and this makes the stretchability not exhibit. In the portion where the elastic members 35 (45) are cut and discontinuous in this way, the elastic members 35 (45) each contract and become thicker in outer diameter, so that the elastic members 35 (45) are more likely to be caught by the welded portion pair 50s. Therefore, rubber coming off etc. are likely to be suppressed, and the stretchability is less likely to deteriorate. In addition, providing the discontinuous portion makes it possible to partially adjust the strength of stretching/contracting of elastic members, and therefore providing the discontinuous portion in an appropriate portion of the front waist portion 31 (41) can improve the fit of diaper 1.

The diaper 1 may have a portion where at least one pair of the welded portion pair 50s and the absorbent main body 10 overlap when viewed in the front-back (thickness) direction of the diaper 1. Since the absorbent main body 10 has high stiffness, the waist portion 20 is less likely to deform in regions where the waist portion 20 overlaps with the absorbent main body 10 when viewed in the thickness direction, compared to regions where they do not overlap. In the case where the waist portion 20 is able to transform freely, as the waist portion 20 transforms, it increases the distance G50s between the upper welded portion 50a and the lower welded portion 50b, which constitute a pair of the welded portion pairs 50s. This cause a risk that the displacement of the elastic members 35 (45) in the continuous direction or rubber coming off is likely to occur. In contrast, in the regions that overlap with the absorbent main body 10, the waist portion 20 is less likely to deform and the interval G50s of the welded portion pair 50s in the vertical direction is likely to maintain. This makes the damaged portions 37 (47) of the elastic members 35 (45) likely to get caught. That is, the displacement of the elastic members 35 (45) and rubber coming off are less likely to occur. Therefore, nevertheless that the elastic members 35 (45) has the discontinuous portion in the region that overlaps the absorbent main body 10, the stretchability is less likely to deteriorate.

Further, the non-skin-side surface of the back waist portion 41 is provided with a post-handling tape 80, which is used when disposing of used diapers 1 (see FIG. 2). The post-handling tape 80 is a substantially rectangular tape-shaped member (tape member) elongated in the vertical direction, and the one side thereof in the vertical direction is fixed to the back waist portion 41, and to the other side in the vertical direction has an adhesive portion. The adhesive is applied to the adhesive portion 72. Before the diaper 1 is used, a part of the post-handling tape 80 is folded in a state where the adhesive portion inside. Thus, the adhesive portion is not exposed to the outside, protecting the adhesive surface of the adhesive portion. When disposing of the diaper 1 after use, the diaper 1 is rolled in the vertical direction so that the absorbent main body 10 is directed to the inside, and the adhesive portion is exposed by stretching and pulling the folded post-handling tape 80 with respect to the diaper 1. Then, the adhesive portion side is wound around the diaper 1. Therefore, the diaper 1 can be held in a state of being rolled, making it possible to dispose the diaper 1 without outside leaking the excrement or the like which has been attached inside of the diaper 1 (absorbent main body 10).

The diaper 1 may have a portion where at least one pair of the welded portion pair 50s and the post-handling tape 80 overlap when viewed in the thickness direction of the diaper 1. Since the tape member constituting the post-handling tape 80 has high stiffness, the back waist portion 41 is less likely to deform in the region where the post-handling tape 80 is provided, compared to the remaining regions. Therefore, similarly to the above case, in the region that overlaps with the post-handling tape 80, the interval G50s of the welded portion pair 50s in the vertical direction is likely to maintain, and the damaged portions 37 (47) of the elastic members 35 (45) get caught in the welded portion pair 50s, making the elastic members 35 (45) less likely to come off. This suppresses the deterioration of the stretchability.

Figure 13:
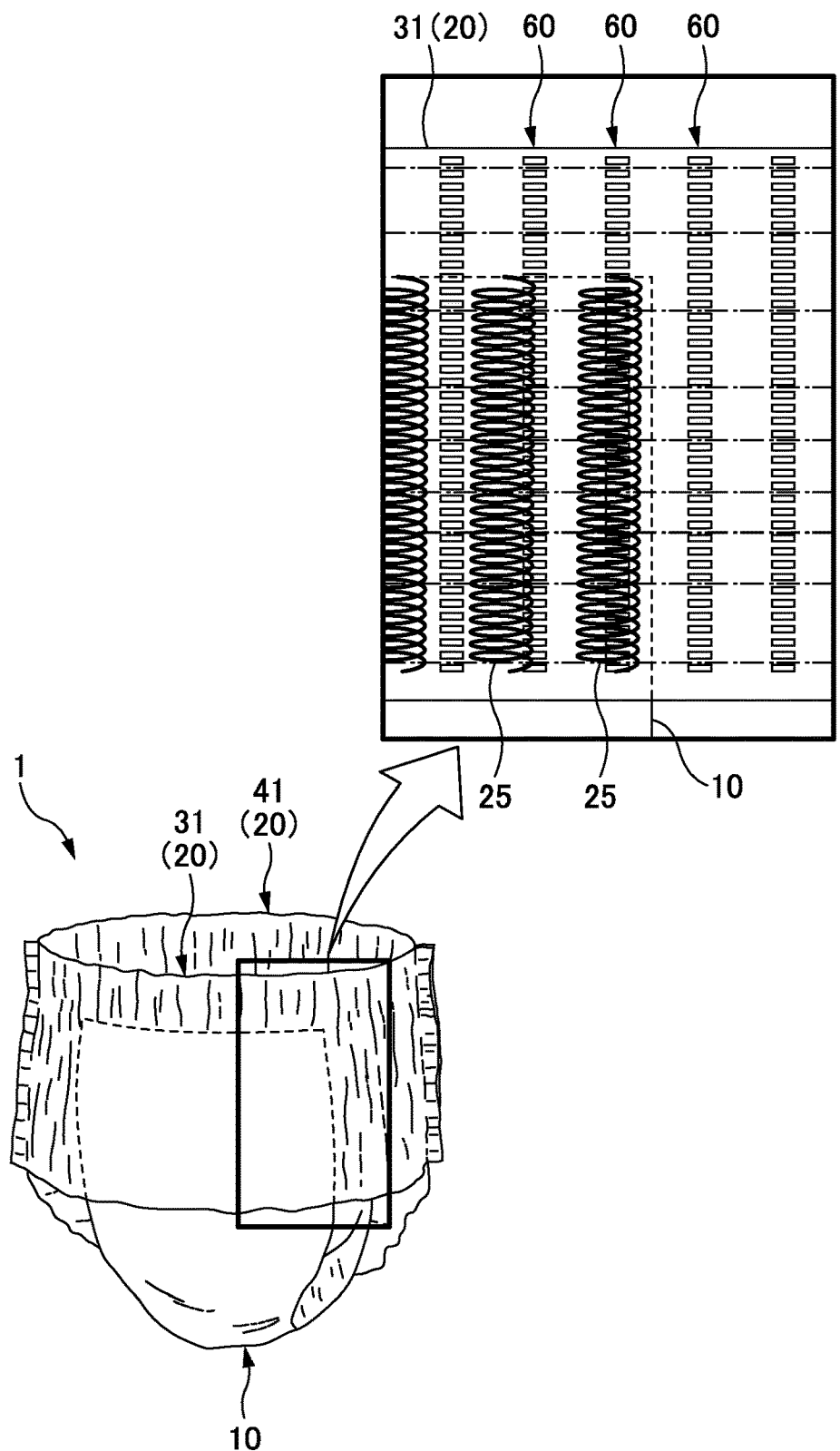
FIG. 13 is a partially enlarged view illustrating the arrangement of main-body joining portions that connect the waist portion and the absorbent main body.

FIG. 13 is a partially enlarged view illustrating the arrangement of main-body joining portions 25 that connect the waist portion 20 and the absorbent main body 10. FIG. 13 shows a portion where the front waist portion 31 and the absorbent main body 10 are joined, and also the joining of the back waist portion 41 and the absorbent main body 10 is made via the main-body joining portions 25 in substantially the same way as on the front side.

The main-body joining portions 25 are formed as follow: the adhesive such as the hot-melt adhesive is applied to a predetermined region between the non-skin-side surface of the absorbent main body 10 (the back sheet 15) and the skin-side surface of the front waist portion 31 (the second sheet 32) (see FIG. 3), and the front waist portion 31 (41) and the absorbent main body 10 are connected to each other by the main-body joining portion 25. In FIG. 13, a spiral main-body joining portion 25 is formed along the vertical direction, but the arrangement and shape of the main-body joining portion 25 are not limited to this. For example, the main-body joining portion 25 may be formed by applying the adhesive in a band shape or an Q-shape, or the main-body joining portion 25 may be formed along the lateral direction.

The diaper 1 may have a portion where at least one pair of the welded portion pair 50s and the main-body joining portion 25 overlap when viewed in the thickness direction of the diaper 1. In the portions where the main-body joining portion 25 is provided, the stiffness of the waist portion 20 is higher than in the portions where the main-body joining portion 25 is not provided. Therefore, in the welded portion pair 50s, which is placed overlapping the main-body joining portion 25, the interval G50s in the vertical direction is less likely to spread, and the damaged portions 37 (47) of the elastic members 35 (45) get caught in the welded portion pair 50s, making the elastic members 35 (45) less likely to come off. This makes it likely to suppress the deterioration of the stretchability in the waist portion 20.

Furthermore, at least the main-body joining portion 25 and two of the welded portion pairs 50s may overlap with respect to the vertical direction (intersecting direction). With such a configuration, it is likely to maintain the relative positions of at least two welded portion pairs 50s with respect to the vertical direction, making it less likely to cause the displacement of the elastic member 35 (45) in the vertical direction. Therefore, in stretchability due to the elastic members 35 (45), a difference between the upper side and the lower side in the vertical direction is less likely to occur, enabling to make it less likely to cause distortion when the waist portion 20 stretches and contracts.

Further, at least two of the welded portion pairs 50s and the main-body joining portion 25 may overlap with respect to the lateral direction (continuous direction). With such a configuration, the damaged portions 37 (47) of the elastic members 35 (45) is likely to be caught in at least two welded portion pairs 50s in the lateral direction. This makes it more likely to suppress the displacement of the elastic members 35 (45) in the continuous direction, and enabling to make the stretchability of the waist portion 20 less likely to deteriorate.

Second Example

Figure 14:
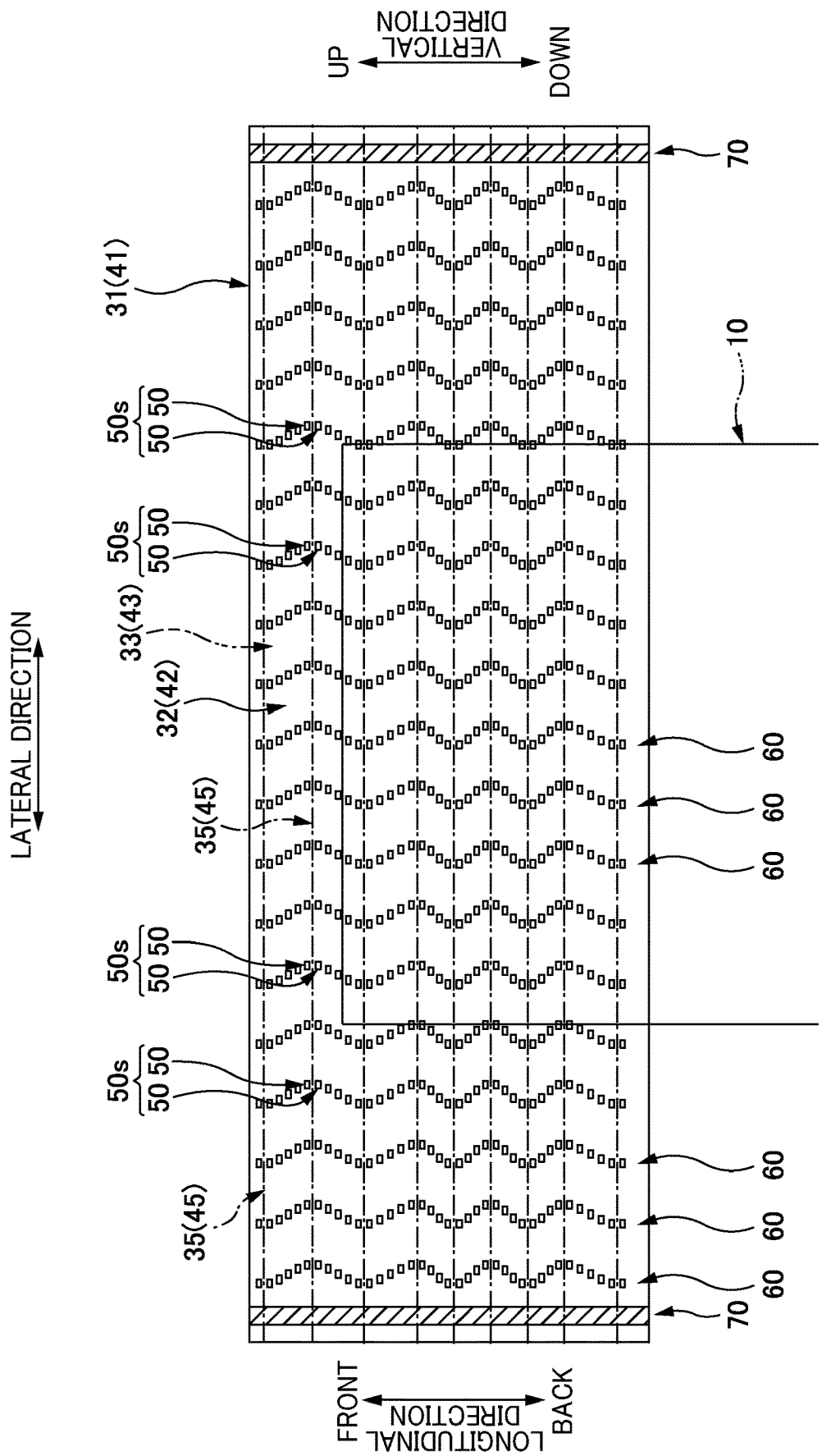
FIG. 14 is a diagram illustrating the shape and arrangement of welded portions of the second example.

In the second example, an example will be described in which the arrangement of the welded portions 50 provided in the front waist portion 31 and the back waist portion 41 are different from the first example. FIG. 14 is a diagram illustrating the shape and arrangement of the welded portions 50 of the second example, and corresponds to FIG. 4 of the first example. Note that the basic configuration of the disposable diaper of the second example is substantially the same as the diaper 1 of the first example, and only the arrangement of the welded portions 50 is different from that of the diaper 1.

In the second example, the welded portions 50 provided in the front waist portion 31 and the back waist portion 41 form welded portion rows 60 that meander in the lateral direction, as shown in FIG. 14. In other words, two welded portions 50 and 50 adjacent in the vertical direction are arranged so that their portions are located being shifted from each other in the lateral direction, and this makes the welded portions form convex parts on both sides in the lateral direction. However, the shape s of the welded portion rows is not limited to that shown in FIG. 14, and the arrangement of each welded portion 50 is not limited to the example shown in FIG. 14. For example, the welded portion rows may have convex portions only on the one side in the lateral direction.

By changing the arrangement of the welded portion rows 60 in this way, it is possible to adjust wrinkles formed on the surfaces of the front waist portion 31 and the back waist portion 41. For example, by making the welded portion rows 60 meander in the lateral direction as shown in FIG. 14, it makes irregular the shape and size of the wrinkles formed between two welded portion rows 60 and 60 adjacent in the lateral direction, making it possible to make soft the texture of the front waist portion 31 (41) and to make it easier to create a natural texture.

In the second example, as well as the first example, the damaged portion 37 (47) where a part of the surface of the elastic member 35 (45) has been damaged is provided between the first welded portion pair 51s and the second welded portion pair 52s, which are located adjacent to each other in the lateral direction of the front waist portion 31 (41). With such a configuration, by making the damaged portion 37 (47) get caught in either of the first welded portion pair 51s and the second welded portion pair 52s, it suppresses the displacement of the elastic member 35 (45) in the continuous direction, making it possible to prevent the stretchability of the front waist portion 31 (41) (the stretchable sheet) from deteriorating.

Other Embodiments

Although the embodiments of the present disclosure have been described hereinabove, the above embodiments of the present disclosure are simply to facilitate understanding of the present disclosure and are not in any way to be construed as limiting the present disclosure. The present disclosure may variously be changed or altered without departing from its gist and encompass equivalents thereof. For example, modified examples which will be described below are possible.

Continuous Direction of Elastic Members 35, 45

In the above-mentioned embodiments, for the stretchable sheet, which constitutes the front waist portion 31 and the back waist portion 41 of diaper 1, the continuous direction of the elastic members 35 and 45 is parallel to the lateral direction of diaper 1. In other words, the elastic members 35 and 45 are configured to stretch and contract along the lateral direction of the diaper 1, but at least some of the elastic members 35 and 45 may be configured to stretch and contract along the direction tilted with respect to the lateral direction of the diaper 1.

Figure 15:
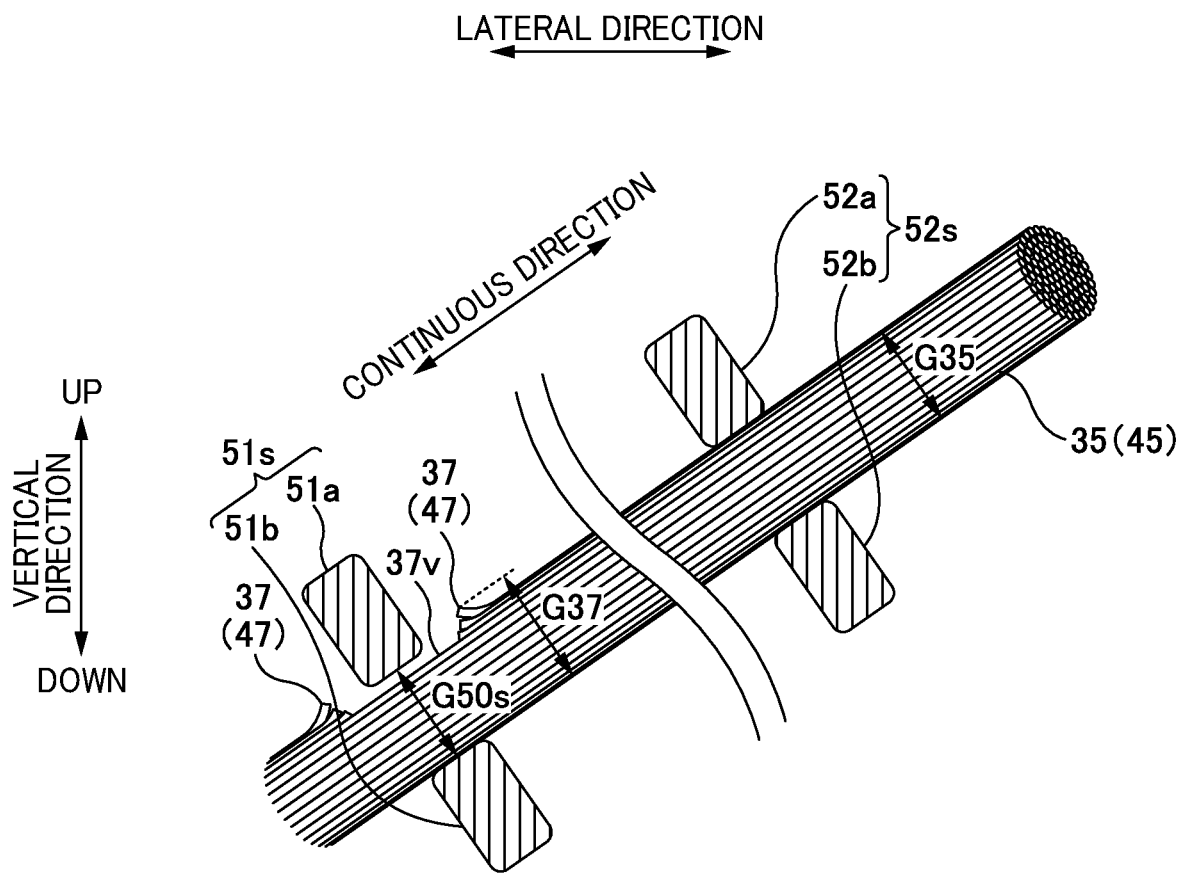
FIG. 15 is a diagram showing an example of a relationship between the continuous direction of the elastic member and the lateral direction of the diaper.

FIG. 15 is a diagram showing an example of a relationship between the continuous direction of the elastic member 35 (45) and the lateral direction of the diaper 1. In FIG. 15, the continuous direction of the elastic member 35 (45) is a direction inclined with respect to the lateral direction of the diaper 1. With such a configuration, the elastic member 35 (45) can exhibit the stretchability in a direction inclined at a predetermined angle with respect to the lateral direction of diaper 1 (that is, diagonally). For example, the back waist portion 41 of the diaper 1 has the buttocks cover 41c which has a substantially trapezoidal shape in the lower end portion in the vertical direction (see FIG. 2). Since the peripheral edge of the buttocks cover 41c is cut diagonally, in order for the buttocks cover to fit perfectly on the wearer's buttocks during usage of the diaper 1, the stretchability may act along the peripheral edge of the buttocks cover 41c. In such a case, the elastic members 35 (45) may be arranged so that their continuous direction is inclined to the lateral direction as shown in FIG. 15. That is, in the back waist portion 41 in FIG. 2, the elastic members 45 are arranged extending from the lower end portion of the side joining portion 70 inward in the lateral direction and downward in the vertical direction. This makes it possible for the stretchability due to the elastic members 45 to be exhibited along the slope of the peripheral edge of the buttocks cover 41c.

Titanium Oxide Contained in the Elastic Member 35, 45

In the above-mentioned embodiments, the elastic member 35 may contain the titanium oxide. Specifically, the elastic members 35 may have the titanium oxide less than 3.0% of the content rate, or 0.1% or more and less than 3.0%. By including such a small amount of the titanium oxide, the surface of the elastic member 35 can be made uneven, and this improves the unwinding reelability, and also stabilizes the running performance of the elastic member 35 in processing machines. When a large amount of metal oxides such as titanium oxide are included in polyurethane-based spandex yarn and the like (synthetic fiber), the yarn becomes hard, and accordingly in the case of forming the damaged portions 37 (where a part of the surface of the continuous body of the elastic member 35 is damaged) in the joining step of the manufacturing method for the stretchable sheet, the continuous body of the elastic member 35 becomes likely to break. But, by setting the content rate as above, it is possible to provide an appropriate damaged portions 37, enabling to prevent the deterioration of the stretchability of the stretchable sheet, which is caused by breaking completely to make the elastic member 35 discontinuous. In addition, even in the case where the outer diameter G35 of the elastic member 35 is smaller than the interval G50s of the welded portion pair 50s in the intersecting direction as shown in FIG. 9, the damaged portion 37 can be stably provided on the rubber, and therefore the damaged portion 37 of the elastic member 35 is likely to be caught and tightly held between the welded portion pair 50s without the adhesive. Therefore, it is likely to further prevent the displacement of the elastic member 35 in the continuous direction, and it is possible to make it less likely for the stretchability of the waist portion to deteriorate.

In addition, the content rate of the titanium oxide of the elastic member 35 can be obtained as follows. First, a sample is decomposed with sulfuric acid based on the pressure sulfuric acid decomposition method of JIS R 9301-3-4 Alumina powder-Part 3: Methods of chemical analysis-4: Decomposition by acid in pressure vessel, and a sample solution is prepared. Next, a part of the prepared sample solution is measured by Inductively Coupled Plasma-Optical Emission Spectrometry (ICP-OES) based on JIS R 9301-3-7 Alumina powder-Part 3: Methods of chemical analysis-7: Determination of titanium oxide (IV) content, quantifying titanium. This quantified amount of titanium is converted to that of titanium dioxide. Then, the content rate is calculated based on the quantified titanium dioxide. Note that the above measurement may be performed by Inductively Coupled Plasma-Mass Spectrometry (ICP-MS) in addition to Inductively Coupled Plasma-Optical Emission Spectrometry.

Wrinkles Formed on Surface of Stretchable Sheet

When the stretchable sheet that can stretch and contract in the continuous direction contracts from the stretched state, a plurality of wrinkles protruding in the thickness direction are formed on the surface of the stretchable sheet. Then, when the wrinkles protruding in the thickness direction fall in the continuous direction, a part of the surface of the stretchable sheet is covered by the wrinkles. In particular, if the welded portion pair 50s holding the elastic member 35 (45) is covered with fallen wrinkles, the elastic member 35 (45) may be less likely to be visually recognized from the outside. In this case, a user is less likely to recognize the exhibition of the stretchability due to the elastic member 35 (45), and there is a risk that the user has an anxiety about the stretchability of the stretchable sheet. Therefore, by configuring the stretchable sheet as follows, the user can easily recognize the stretchability.

Figures 16A, 16B:
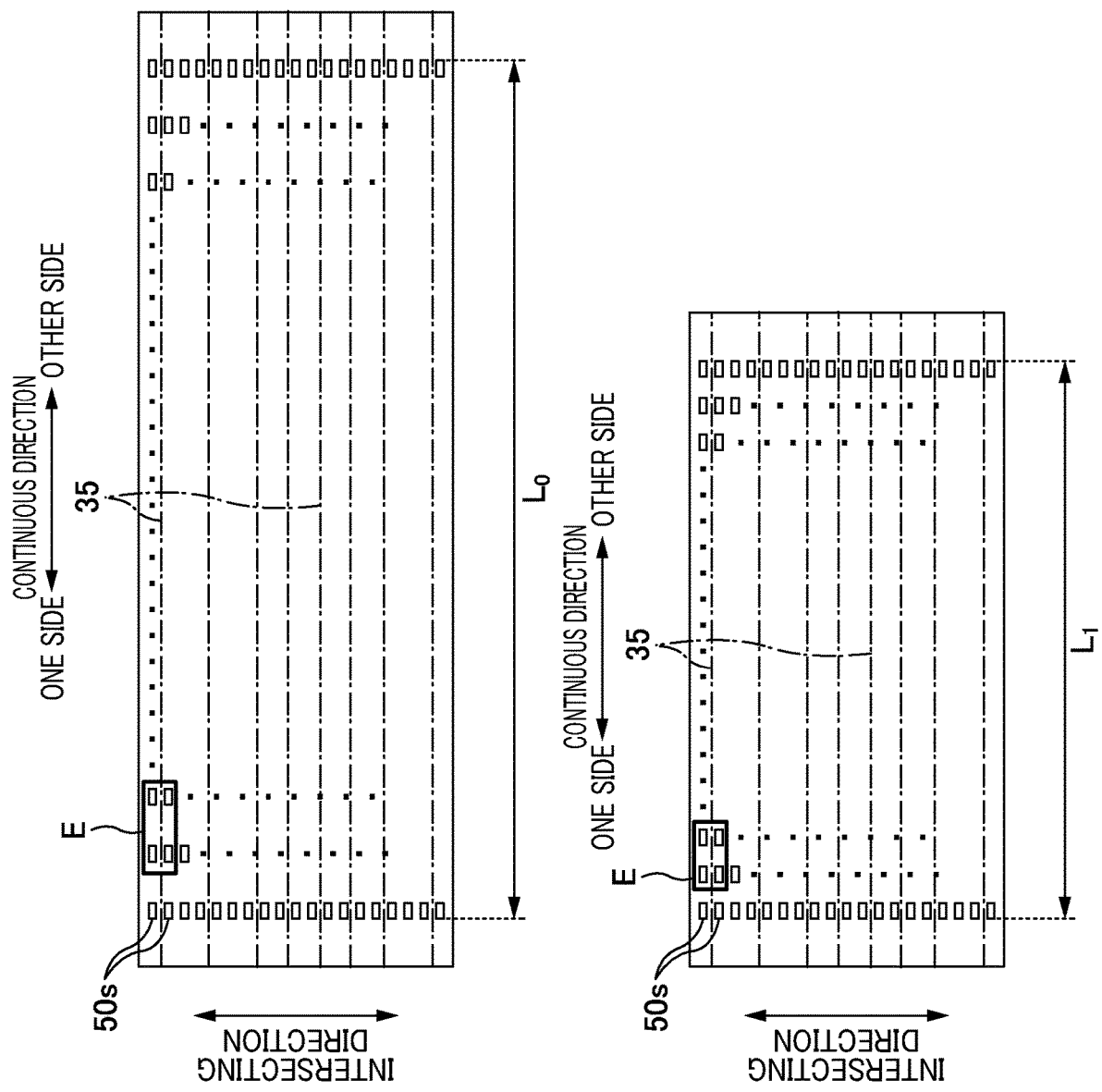
FIG. 16A is a schematic plan view illustrating the stretchable sheet in the stretched state.
FIG. 16B is a schematic plan view illustrating a state where the stretchable sheet in FIG. 16A contracts (a natural state).
Figure 17A:
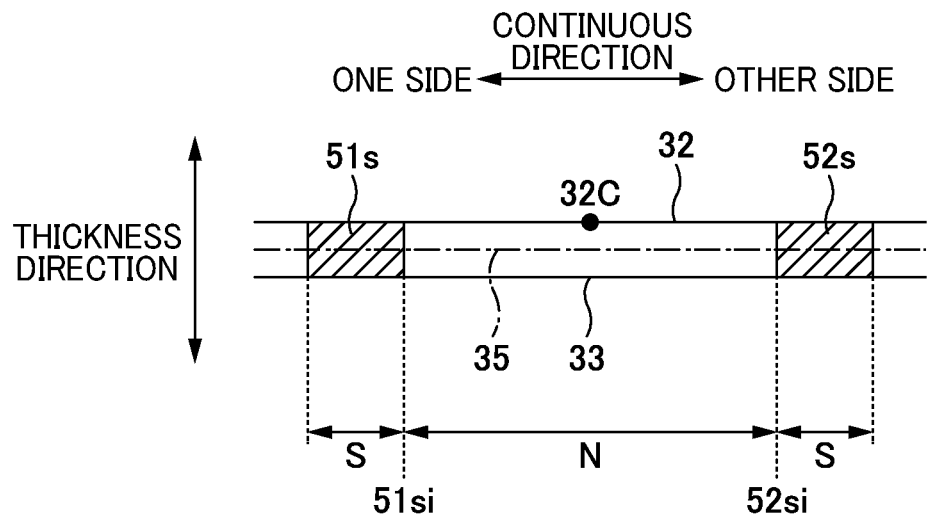
FIG. 17A is a schematic cross-sectional view of a region in FIG. 16A when viewed in an intersecting direction.
Figure 17B:
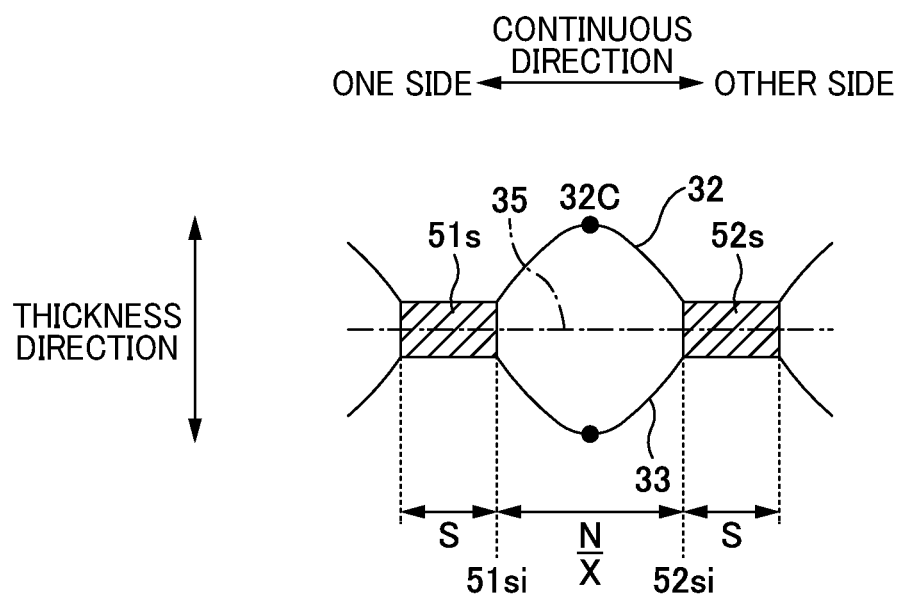
FIG. 17B is a schematic cross-sectional view of a region in FIG. 16B when viewed in the intersecting direction.

FIG. 16A is a schematic plan view illustrating the stretchable sheet (e.g., the waist portions 31 and 41) in the stretched state. FIG. 16B is a schematic plan view illustrating a state where the stretchable sheet in FIG. 16A contracts (the natural state). In FIGS. 16A and 16B, it is assumed that a plurality of the elastic members 35 are provided extending along the continuous direction (lateral direction), and the stretchable sheet stretches and contracts in the continuous direction. Further, in FIGS. 16A and 16B, some of the welded portion pairs 50s are not displayed. FIG. 17A is a schematic cross-sectional view of the region E in FIG. 16A when viewed in the intersecting direction. FIG. 17B is a schematic cross-sectional view of a region E in FIG. 16B when viewed in the intersecting direction.

In the stretchable sheet that is in the stretched state shown in FIG. 16A, let $L_0$ be the continuous-direction length of the region where the stretchability due to the elastic member 35 acts. That is, $L_0$ is the distance from the welded portion pair 50s which is located farthest on the one side in the continuous direction of the stretchable sheet and which holds the elastic member 35 in between, to the welded portion pair 50s which is located farthest on the other side and which holds the elastic member 35 in between. Note that in cases such as when the stretch factor in the continuous direction is changing within the stretchable sheet, the measurement region can be selected as appropriate.

Also, as shown in FIG. 17A, in the continuous direction of the stretchable sheet that is in the stretched state, of the two adjacent welded portion pairs 50s and 50s, the one provided on the one side in the continuous direction is a first welded portion pair 51s and the one provided on the other side in the continuous direction is a second welded portion pair 52s. At this time, in the continuous direction, the distance (length) between the inner end (other-side end) 51si of the first welded portion pair 51s and the inner end (one-side end) 52si of the second welded portion pair 52s is defined as a length N, and the length of the welded portion pair 50s (51s, 52s) is defined as a length S.

As mentioned above, in the stretchable sheet, the first sheet 32 and the second sheet 33, which are overlaid in the thickness direction, are joined by the plurality of welded portions 50, 50, . . . , and the elastic members 35 that are provided between the first sheet 32 and the second sheet 33 in the thickness direction are sandwiched between two welded portions 50 and 50 (that is, the welded portion pair 50s) adjacent to each other in the intersecting direction. Therefore, in the stretchable sheet that is in the stretched state, the lengths of the first sheet 32, second sheet 33 and elastic members 35 in the continuous direction all are N between the inner ends (51si, 52si) of two welded portion pairs 51s and 52s that are adjacent in the continuous direction (see FIG. 17A). Further, in the first sheet 32, the center position between the welded portion pairs 51s and 52s (the inner ends 51si and 52si) in the continuous direction is indicated by 32C.

When the stretchable sheet in FIG. 16A contracts in the continuous direction and becomes in the natural state shown in FIG. 16B, the distance in the continuous direction of the stretchable sheet between the located-farthest-on-one-side welded portion pair 50s which holds an elastic member 35 and the located-farthest-on-other-side welded portion pair 50s which holds the elastic member 35 is $L_1$. That is, if the stretch factor of the stretchable sheet in the continuous direction is X, then it is expressed as $X=L_0/L_1$.

Then, in the stretchable sheet that is in the natural state, the distance in the continuous direction between the inner ends 51si and 52si of two adjacent welded portion pairs 51s and 52s is N/X (see FIG. 17B). At this time, the elastic members 35 contract along the continuous direction, whereas the first sheet 32 and the second sheet 33 are made of the nonwoven fabric having a lower stretchability. Therefore, in the first sheet 32 and the second sheet 33, without contracting along the continuous direction, the convex deformation occurs between the welded portion pairs 51s and 52s in the thickness direction as shown in FIG. 17B. The portions where the convex deformation occurs are connected in the intersecting direction, and thereby wrinkles extending in the intersecting direction are formed on the surface of the stretchable sheet.

FIG. 17B shows an example in which the convex deformation occurs in the first sheet 32, into a substantially isosceles triangle shape with the apex being the center position 32C between the welded portion pairs 51s and 52s adjacent in the continuous direction. Further, in FIG. 17B, the length of the welded portion pair 50s in the continuous direction is considered to be equal to the length S of the welded portion pair 50s in the stretched state. This is because the portion of the stretchable sheet where the welded portion pair 50s is provided has high stiffness and is less likely to contract in the continuous direction, so the amount of change in the length S of the welded portion pair 50s between the stretched state and the natural state is small enough to be ignored.

Figure 18:
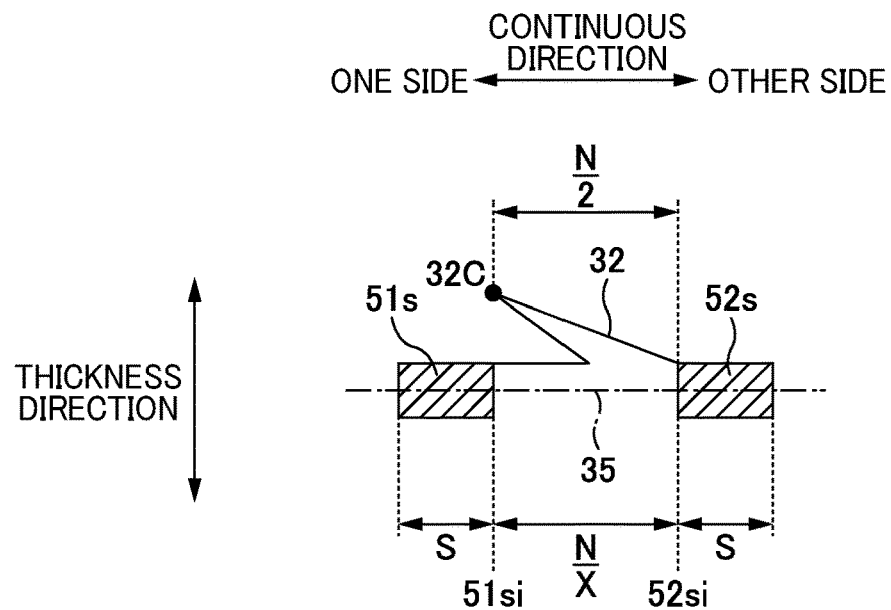
FIG. 18 is a schematic cross-sectional view showing a state where a portion of a first sheet which has deformed protruding in the thickness direction falls in the continuous direction.

The wrinkles formed on the surface of the stretchable sheet that is in the natural state do not always maintain a state of convex deformation in the thickness direction (see FIG. 17B), and the portion where the convex deformation (wrinkles) may fall in the continuous direction. FIG. 18 is a schematic cross-sectional view showing a state where a portion of the first sheet 32 which has deformed protruding in the thickness direction falls in the continuous direction.

FIG. 18 shows a case where the wrinkle formed in the first sheet 32 falls toward the one side in the continuous direction with the center position 32C as the apex. At this time, in the continuous direction, the distance between the inner end (one-side end) 52si of the second welded portion pair 52s provided on the other side and the center position 32C of the first sheet 32 that has fallen toward the one side is expressed as N/2. In addition, in FIG. 18, the straight line connecting the center position 32C of the first sheet 32 and the inner end (one-side end) 52si of the second welded portion pair 52s is drawn obliquely with respect to the continuous direction. In other words, the wrinkles are drawn fallen diagonally. However, in the present description, for the sake of convenience in explaining the magnitude of the influence when the wrinkles fall down, it is be assumed that the wrinkles have fallen down until they become parallel to the continuous direction.

Figure 19A:
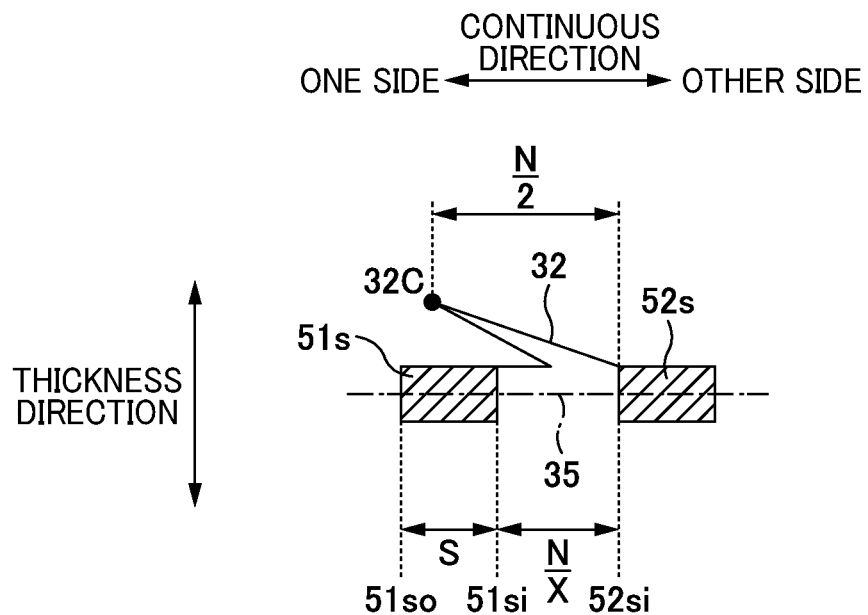
FIG. 19A is a schematic cross-sectional view illustrating the influence of the size of wrinkles formed in the first sheet.
Figure 19B:
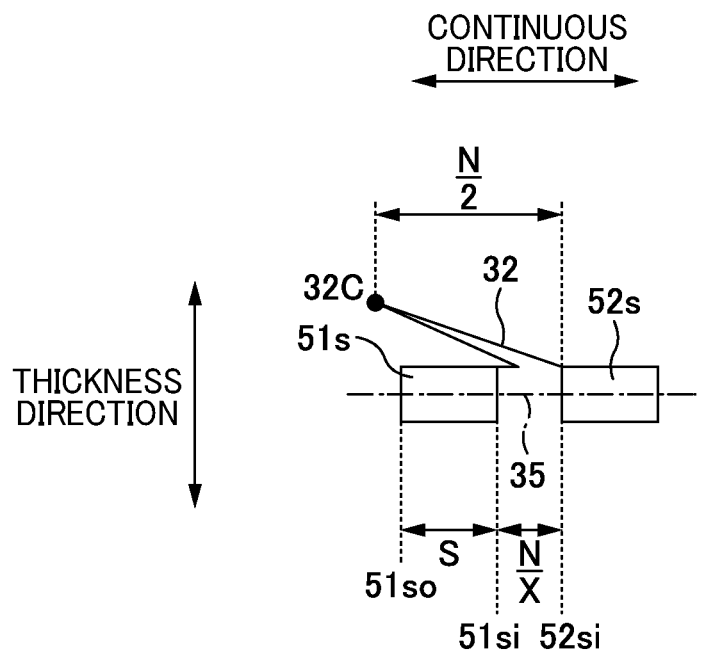
FIG. 19B is a schematic cross-sectional view illustrating the influence of the size of wrinkles formed in the first sheet.

FIGS. 19A and 19B are schematic cross-sectional views illustrating the influence of the size of wrinkles formed in the first sheet 32, and are diagrams corresponding to FIG. 18. In FIG. 19A, in the stretchable sheet that is in the natural state, a wrinkle formed in the first sheet 32 falls down toward the one side in the continuous direction, and as a result, a part of the first welded portion pair 51s overlaps the fallen wrinkle in the thickness direction. That is, FIG. 19A shows a case where, in the continuous direction, the center position 32C of the first sheet 32 is located on the other side with respect to the one-side end 51so of the first welded portion pair 51s. In other words, FIG. 19A shows a case where the distance in the continuous direction between the one-side end 52si of the second welded portion pair 52s and the center position 32C of the first sheet 32 (=N/2) is shorter than the distance in the continuous direction between the one-side end 52si of the second welded portion pair 52s and the one-side end 51so of the first welded portion pair 51s (=S+N/X) (N/2<S+N/X).

Next, FIG. 19B shows a state where, in the stretchable sheet that is in the natural state, the wrinkle formed in the first sheet 32 has fallen toward the one side in the continuous direction, and as a result, the entirety of the first welded portion pair 51s has overlapped with the fallen wrinkle in the thickness direction. In other words, FIG. 19B shows a case where, in the continuous direction, the center position 32 of the first sheet 32 is located on the one side with respect to the one-side end 51so of the first welded portion pair 51s. In other words, FIG. 19B shows a case where the distance in the continuous direction between the one-side end 52si of the second welded portion pair 52s and the center position 32 of the first sheet 32 (=N/2) is longer than the distance in the continuous direction between the one-side end 52si of the second welded portion pair 52s and the one-side end 51so of the first welded portion pair 51s (=S+N/X) (N/2>S+N/X).

In the case of FIG. 19B, when the stretchable sheet with the wrinkles collapsed is viewed in the thickness direction, the first welded portion pair 51s is no longer visible because the entirety of the first welded portion pair 51s is covered by the wrinkles (first sheet 32). Therefore, the elastic member 35 which is held between the first welded portion pair 51s is also no longer visible from the outside. In this case, a user is less likely to recognize the exhibition of the stretchability due to the elastic member 35, and there is a risk that the user has an anxiety about the stretchability of the stretchable sheet.

In contrast, in the case of FIG. 19A, since at least a portion of the first welded portion pair 51s is not covered by the wrinkles (first sheet 32), the portion of the first welded portion pair 51s that is not covered by the wrinkles is visible. For example, in FIG. 19A, the first welded portion pair 51s is visible in a portion between one-side end 51so of the first welded portion pair 51s and the center position 32 of the first sheet 32, making a part of the elastic member 35 sandwiched by the first welded portion pair 51s also visible. In this case, the user recognizes the exhibition of the stretchability due to the elastic member 35, making it likely to recall the stretchability of the stretchable sheet.

In addition, in the continuous direction, in the case where the center position 32 of the first sheet 32 is located in the same position as the other-side end 51si of the first welded portion pair 51s or located on the other side with respect to the other-side end 51si (N/2≤N/X), the entirety of the first welded portion pair is no longer covered by wrinkles, and this makes the entirety of the first welded portion pair 51s visible, making the elastic member 35 most likely to be seen.

Further, in order to further enhance the visibility of the elastic members 35, the elastic members 35 are colored in a different color between the first sheet 32 and the second sheet 33. This makes the user likely to recognize the exhibition of the stretchability due to the elastic member 35, and making it likely to recall the stretchability of the stretchable sheet.

From these facts, in the case where a wrinkle is formed by the first sheet 32 (second sheet 33) when the stretchable sheet contracts and the formed wrinkle falls in the continuous direction, if the condition (N/2≤N/X) is satisfied, the elastic members 35 each of which is sandwiched between the welded portion pair 50s becomes most likely to be visually recognized. That is, if the following Equation (1) is satisfied, the elastic members 35 becomes likely to be visually recognized.

$$X \leq 2 \tag{1}$$

Further, if the condition (N/2<S+N/X) is satisfied, at least a part of the elastic member held between the welded portion pair 50s becomes visible. That is, if the following Equation (2) is satisfied, the elastic member 35 becomes visible.

$$S > \frac{N}{2} - \frac{N}{X} \tag{2}$$

Therefore, if there is a portion of the stretchable sheet that satisfies either one of Equation (1) and Equation (2) described above, this makes it likely to prevent the welded portion pair from being completely covered with fallen wrinkles compared to the case where Equation (1) and Equation (2) are not satisfied. Therefore, at least a part of a portion of the colored elastic member that is sandwiched between the welded portion pair 50s is made likely to be seen from the outside in the thickness direction, enabling to make the user likely to recognize that, in the stretchable sheet, the stretchability due to the elastic members 35 act.

Figure 20A:
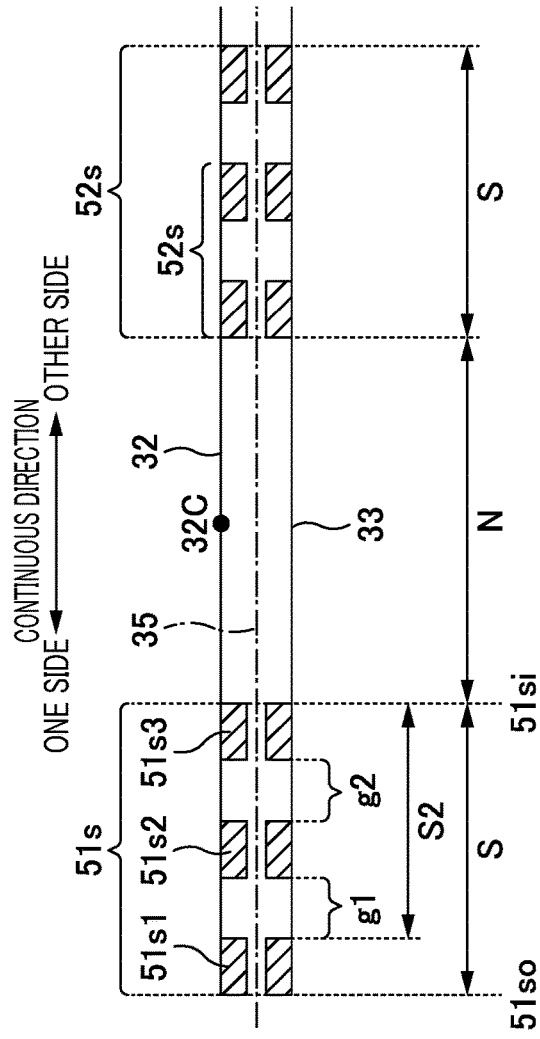
FIG. 20A is a schematic cross-sectional view illustrating the influence of the size of wrinkles formed in the first sheet when the welded portion pair is divided.
Figure 20B:
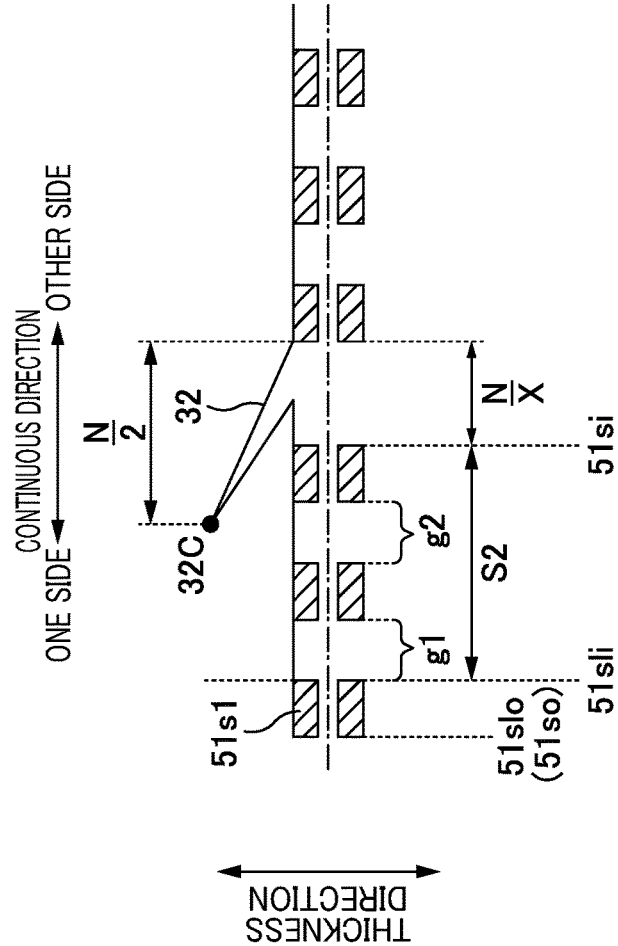
FIG. 20B is a schematic cross-sectional view illustrating the influence of the size of wrinkles formed in the first sheet when the welded portion pair is divided.

Next, a case where the welded portion pair 50s is divided into two or more parts in the continuous direction will be described as a modified example. FIGS. 20A and 20B are schematic cross-sectional views illustrating the influence of the size of wrinkles formed in the first sheet 32 when the welded portion pair 50s is divided. FIG. 20A is a schematic cross-sectional view illustrating the welded portion pair 50s of the stretchable sheet that is in the stretched state, when viewed in the intersecting direction, and FIG. 20B is a schematic cross-sectional view in a state where the stretchable sheet has contracted in the continuous direction from the state in FIG. 20A (the natural state).

In FIG. 20A, similarly to FIG. 17A, there are provided the first welded portion pair 51s and the second welded portion pair 52s that is arranged adjacent to and on the one side in the continuous direction with respect to the first welded portion pair 51s. Then, the first welded portion pair 51s is divided into three in the continuous direction by two notched portions g1 and g2. In other words, the first welded portion pair 51s is divided into three: an outer first welded portion pair 51s1, which is located farthest on the one side in the continuous direction; an inner first welded portion pair 51s3, which is located farthest on the other side; and a middle first welded portion pair 51s2, which is located between the outer first welded portion pair 51s1 and the inner first welded portion pair 51s3 in the continuous direction. Similarly, the second welded portion pair 52s is also divided into three by the notched portions g1 and g2.

In addition, in FIG. 20A, the first welded portion pair 51s is divided into three in the continuous direction by the two notched portions g1 and g2, but the division of the first welded portion pair 51s is not limited to this. For example, the first welded portion pair 51s may be divided into two in the continuous direction by one notched portion, or the first welded portion pair 51s may be divided into four or more in the continuous direction by three or more notched portions.

In addition, in FIG. 20A, letting S be the length of the first welded portion pair 51s in the continuous direction, and letting S1 be the length of the outer first welded portion pair 51s1 in the continuous direction, the value obtained by subtracting the length (S1) of the outer first welded portion pair 51s1 in the continuous direction from the length (S) the first welded portion pair 51s in the continuous direction is set to S2 (S2=S−S1). That is, S2 represents the total length of the inner first welded portion pair 51s3, the middle first welded portion pair 51s2, the notched portion g1, and the notched portion g2 in the continuous direction.

When the stretchable sheet contracts in the continuous direction from the stretched state in FIG. 20A and becomes in the natural state, the first sheet 32 deforms in a convex manner in the thickness direction, and a wrinkle is formed with the center position 32c at the top, similar to what is described in FIG. 17B. Then, when the wrinkle has fallen toward the one side in the continuous direction, the first welded portion pair 51s may be covered by the wrinkle (first sheet 32) in the thickness direction, as shown in FIG. 20B.

At this time, in the continuous direction, if the center position 32c of the first sheet 32 is located on the other side with respect to the other-side end 51s1i of the outer first welded portion pair 51s1 in the continuous direction, at least the outer first welded portion pair 51s1 is not covered by the wrinkle (first sheet 32), making visible the elastic member 35 which is sandwiched between the outer first welded portion pair 51s1. That is, in the continuous direction, the distance (=N/2) between the one-side end 52si of the second welded portion pair 52s and the center position 32C of the first sheet 32 is shorter than the distance (S2+N/X) between the one-side end 52si of the second welded portion pair 52s and the other-side end 51s1i of the outer first welded portion pair 51s1 in the continuous direction (N/2<S2+N/X), at least a part of the elastic member 35 is visible. In addition, the distances of the two notched portions g1 and g2 in the continuous direction hardly change before and after stretching and contraction, and therefore it is assumed that the length S (S2) of the first welded portion pair 51s in the continuous direction also does not change before and after stretching and contraction.

Therefore, in the case of the stretchable sheet related to the foregoing embodiments, if the welded portion pair 50s is divided by the notched portion in the continuous direction, further satisfying the Equation (3) makes it likely to visually recognize the elastic member 35 that is sandwiched between the welded portion pair 50s (outer first welded portion pair 51s1), compared to the case where the condition of Equation (3) is not satisfied.

$$S2 > \frac{N}{2} - \frac{N}{X} \tag{3}$$

In addition, in the notched portions g1 and g2 formed in the welded portion pair 51s, the elastic member 35 contracts, and it expands in the radial direction (becomes thicker), and this makes it likely to visually recognize the elastic member 35 compared to portions sandwiched between the divided welded portion pairs 51s1 to 51s3. Therefore, the notched portions g1 and g2 may not be covered by the fallen wrinkles (first sheet 32).

In FIGS. 18 to 20, there has been described the case where the wrinkle formed by the first sheet 32 deforming in a convex manner in the thickness direction falls down with the center position 32c in the continuous direction being at the top. But in the case where the wrinkle is actually formed, the wrinkle does not necessarily fall with the center position 32c at the top. Therefore, the following describes a case where the wrinkle falls down the largest in the continuous direction (that is, the case where the fallen wrinkle reaches the farthest position in the continuous direction).

Figure 21:
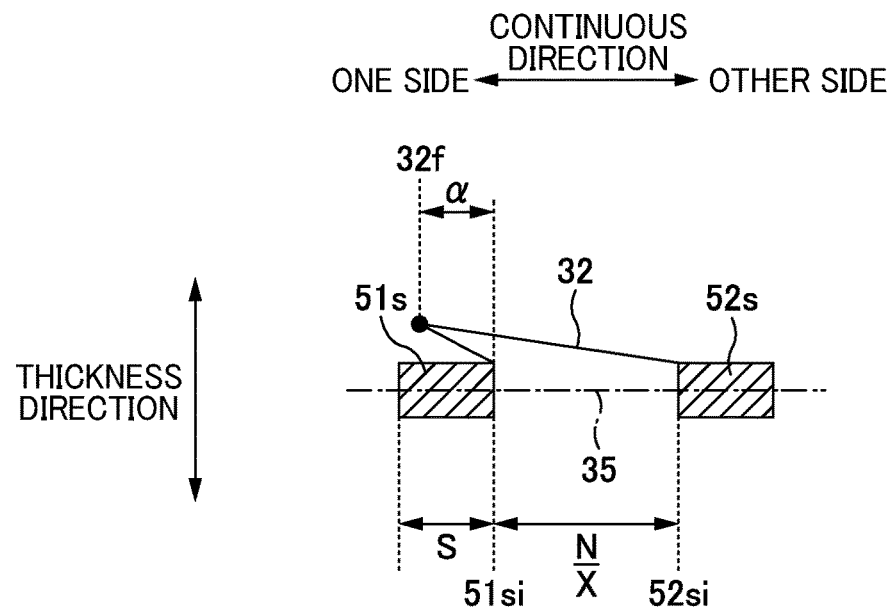
FIG. 21 is a schematic cross-sectional view of a state where the first sheet, which has deformed protruding in the thickness direction, falls down the largest in the continuous direction.

FIG. 21 is a schematic cross-sectional view of a state where the first sheet 32, which has deformed protruding in the thickness direction, falls down the largest in the continuous direction. In FIG. 21, the first sheet 32 falls toward the other side in the continuous direction with the apex being a certain point 32f between the first welded portion pairs 51s and the second welded portion pair 52s. Then, when the apex 32f is located farthest on the one side in the continuous direction, the wrinkles are in a state of falling the largest. That is, in the continuous direction, when the distance between the one-side end 52si of the second welded portion pair 52s and the apex 32f becomes the largest, the wrinkles are in the largest fallen state, making the first welded portion pair 51s likely to be covered by the wrinkles.

At this time, as shown in FIG. 21, if the apex 32f and the one-side end 52si of the second welded portion pair 52s are connected by a straight line, and the apex 32f and the other-side end 51si of the first welded portion pair 51s are connected by a straight line, the apex 32f is located farthest on the one side in the continuous direction. In FIG. 21, letting a be the distance in the continuous direction between the apex 32f and the other-side end 51si of the first welded portion pair 51s, the distance in the continuous direction between the apex 32f and the one-side end 52si of the second welded portion pair 52s is α+N/X. Therefore, when α+(α+N/X) becomes equal to the length N of the first sheet 32 in the stretched state (see FIG. 17A), the apex 32f is located farthest on the one side in the continuous direction (2α+N/X=N).

In FIG. 21, if the length S of the first welded portion pair 51s in the continuous direction is larger than the distance α between the apex 32f and the other-side end 51si of the first welded portion pair 51s (S>α), at least a part of the first welded portion pair 51s is not covered by wrinkles (first sheet 32), and this makes it possible to visually recognize the elastic member 35, which is sandwiched between the first welded portion pair 51e. Here, since α=(N−N/X)/2, the above condition becomes S>(N−N/X)/2

Therefore, in the stretchable sheet according to the foregoing embodiments, in the case where the wrinkles formed in the first sheet 32 fall down the largest, by further satisfying the following Equation (4), the elastic member 35 which is sandwiched by the welded portion pair 50s (first welded portion pair 51s) is likely to be visually recognized.

$$S > \frac{N}{2} - \frac{N}{2X} \qquad (4)$$

Also, there has described to color the elastic member 35 in a different color between the first sheet 32 and the second sheet 33 in order to increase the visibility of the elastic member 35. But it is not necessary that all of the elastic members 35 are colored, and some of the elastic members 35 does not need to be colored. In the case where the stretchable sheet has a region where colored elastic member 35 is arranged and a region where uncolored elastic member 35 is arranged, the arrangement of the elastic members 35 and the arrangement of the welded portion pairs 50S that hold the elastic members 35 may be as follows.

Figure 22A:
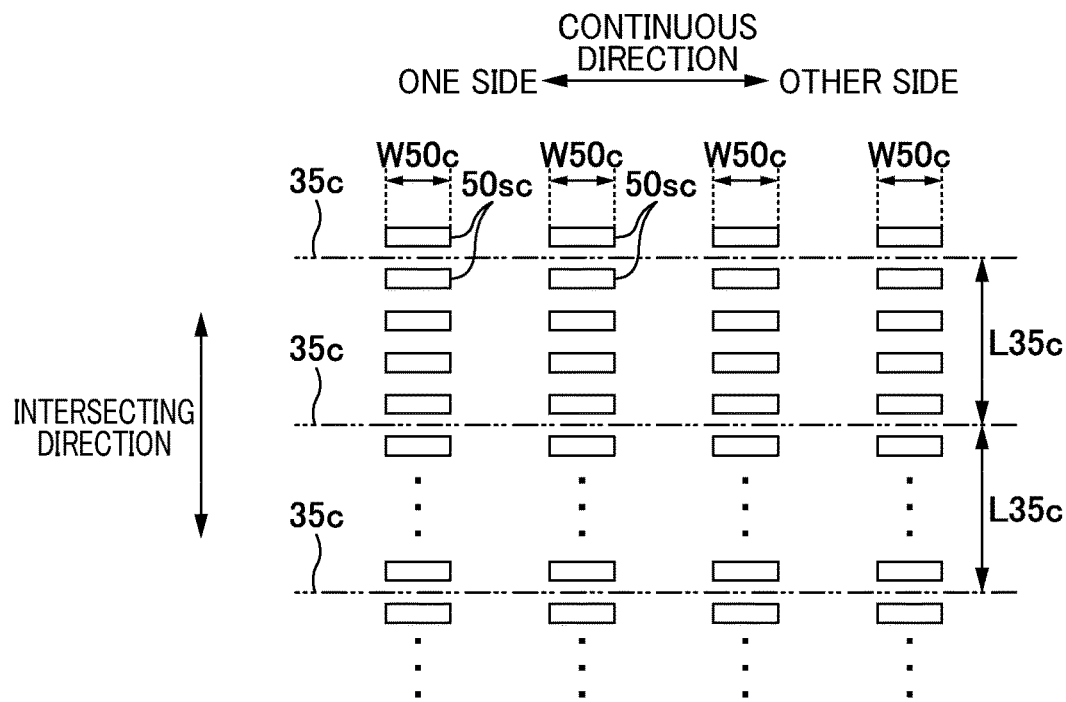
FIG. 22A is a plan view showing a region of the stretchable sheet where the elastic members which are colored in a predetermined color are arranged.
Figure 22B:
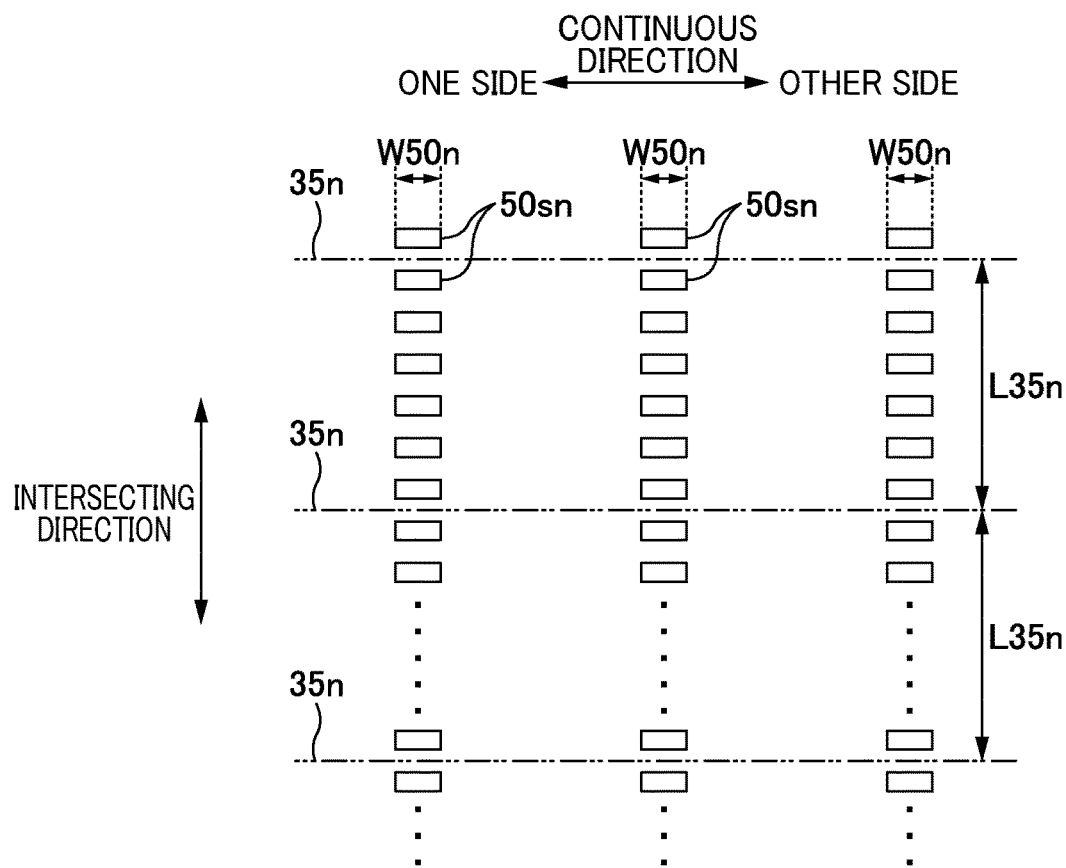
FIG. 22B is a plan view showing a region of the stretchable sheet where the elastic members which are not colored are arranged.

FIG. 22A is a plan view showing a region of the stretchable sheet where the elastic members 35 which are colored in a predetermined color are arranged. FIG. 22B is a plan view showing a region of the stretchable sheet where the elastic members 35 which are not colored are arranged. In FIG. 22A, colored elastic members 35c are arranged extending along the continuous direction and are respectively sandwiched between the welded portion pairs 50sc. In FIG. 22B, the uncolored elastic members 35n are arranged extending along the continuous direction and are respectively sandwiched between the welded portion pairs 50sn.

At this time, in the continuous direction, the sum of the lengths W50c of the welded portion pairs 50sc which are provided in the region where the colored elastic members 35c are arranged (see FIG. 22A) may be longer than the sum of the lengths W50n of the welded portion pairs 50sn which are provided in the region where the uncolored elastic members 35n are arranged (see FIG. 22B).

The longer the length of the welded portion pair 50s in the continuous direction that occupies the region where the elastic members 35 is arranged, the narrower the distance between adjacent welded portion pairs 50s and 50s becomes, making the wrinkles that are formed when the elastic member 35 contracts likely to be smaller. In other words, as described in FIG. 18 etc., in the case where the sheet members 32 and 33 deform in a convex manner and wrinkles are formed between the welded portion pairs 50s and the wrinkles fall, the welded portion pairs 50s are less likely to be covered by the fallen wrinkles. Therefore, by adjusting the total length in the continuous direction for the welded portion pairs 50sc and the welded portion pairs 50sn as described above, the wrinkles formed in the region where colored elastic members 35c are arranged are made smaller than the wrinkles formed in the region where the uncolored elastic members 35n are arranged. The visibility of the elastic members 35c becomes higher in the region where colored elastic members 35c are arranged, enabling to make the user likely to recognize the stretchability.

In addition, as a method for adjusting the total value of the lengths in the continuous direction for the welded portion pairs 50sc and the welded portion pairs 50sn, there is a method of changing the number of welded portion pairs arranged per unit length in the continuous direction between the welded portion pairs 50sc and the welded portion pairs 50sn, or a method of changing the length W50sc and the length W50sn between the welded portion pairs 50sc and the welded portion pairs 50sn.

In addition, the interval (pitch) L35c between the two elastic members 35c and 35c adjacent in the intersecting direction, in the region where the colored elastic members 35c are arranged, may be smaller than the interval (pitch) L35n between two elastic members 35n and 35n adjacent in the intersecting direction, in the region where the uncolored elastic members 35n are arranged. The narrower the pitch of the elastic members 35 in the intersecting direction is, the higher the density in which the elastic member 35 is located, increasing the visibility. Therefore, by making the pitch L35c of colored elastic members 35c in the intersecting direction smaller than the pitch L35n of uncolored elastic members 35n in the intersecting direction, it is possible to make the visibility of the colored elastic members 35c higher than the visibility of the uncolored elastic members 35n. This makes the user likely to recognize the stretchability in the region where the colored elastic members 35c are arranged.

Note that, in the case where the interval (pitch) between two elastic members 35 adjacent in the intersecting direction is not constant, it is recommended to calculate the average interval (pitch) in the intersecting direction between the elastic members 35 located in the target region and to compare.

Further, the nonwoven fabric sheet may include titanium oxide in order to improve aesthetics. It is generally known nonwoven fabric that contains titanium oxide is whitish, but on the other hand, in order to increase the visibility of the colored elastic members which are sandwiched between the nonwoven fabric sheet, it is sufficient to reduce the amount of titanium oxide that is included in the elastic members. By setting the amount of titanium oxide to less than 3.0%, it can make the elastic members likely to be visually recognized.

Further, in the case where the elastic members 35 are colored, the elastic members 35 may have the titanium oxide. As described above, if the content rate of titanium oxide is less than 3.0%, it is possible to make the color of the elastic member 35 likely to be visually recognized. Further, it is sufficient that the content rate of titanium oxide may be of 0.1% to 3.0%. By including a small amount of the titanium oxide, the surface of the elastic member 35 can be made uneven, and this improves the unwinding reelability, and also stabilizes the running performance of the elastic member 35 in processing machines.

Others

In the first sheet 32 and the second sheet 33 that constitute the stretchable sheet, the light transmittance may be 80% or more, or may be 85% or more. With this configuration, the elastic members 35 are more likely to be visually recognized from the outside in the thickness direction (on the surface of the stretchable sheet) through the first sheet 32 and the second sheet 33, enabling to make the user likely to recognize the stretchability of the stretchable sheet.

Furthermore, the light transmittance of nonwoven fabric can be measured as follows based on JIS-K7105. First, a sample piece with a width of 50 mm and a length of 40 mm is taken from the nonwoven fabric to be measured (first sheet 32, second sheet 33). Then, using a commercially available color difference meter (e.g., flicker photometric color difference meter Z-300A manufactured by NIPPON DENSHOKU INDUSTRIES Co., Ltd.), the Tt value (%) of the prepared sample piece is measured and determined as the light transmittance. Note that the power of the color difference meter have to be turned on 30 minutes before the measurement.

Moreover, the length of the welded portion pair 50s in the continuous direction, which sandwiches the elastic member 35 in the intersecting direction, may be 0.5 mm or more and less than 5 mm. By setting the length of the welded portion pair 50s in the continuous direction to 0.5 mm or more, the elastic member 35 sandwiched between the welded portion pair 50s can be more easily visually recognized with the naked eye compared to the case where the length is less than 0.5 mm (e.g., see FIG. 18). On the other hand, by making the length of the welded portion pair 50s in the continuous direction less than 5 mm, it is possible to make the user less likely to feel the hardness due to the tightening of the welded portion pair 50s, compared to the case where it is 5 mm or more.

Further, the elastic member 35 may be a multifilament. The elastic member 35 is constituted by a bundle of fibers, and this makes the elastic member 35 likely to be visually recognized by the user, because, for example, as shown in FIG. 20B, when the elastic member 35 contracts, the elastic member 35 is likely to be thicker in the radial direction due to expansion in the notched portion g of the welded portion pair 50. Accordingly, it is possible to make the user likely to recognize the stretchability.

Moreover, the stretchable sheet may be arranged in a part of the waist portions 31 and 41 of the diaper 1 or a part of the barrier cuff LSG of the absorbent main body 10 (see FIG. 2). By arranging the stretchable sheet including the elastic members 35 having high visibility in predetermined locations of the diaper 1, this makes it likely to recognize the locations where the stretchable sheet is arranged, enabling to make the user likely to recognize that the absorbent article has a good stretchability.

Furthermore, a stretchable sheet in which the colored elastic members 35 are provided may be arranged in either of the front waist portion 31 and the back waist portion 41 in the underpants-shaped diaper 1. With this configuration, the visibility of the stretchable sheet (elastic members 35) on the one side in the front-back direction is higher than the visibility of the stretchable sheet (elastic members 35) on the other side, enabling to make it likely to identify the front-back direction of the diaper 1.

In addition, in the diaper 1, within the first sheet 32 (42) and the second sheet 33 (43) that constitute the waist portion 31 (41), in the case where the first sheet 32 (42) is located on the non-skin side in the thickness direction and the second sheet 33 (43) is located on the skin side in the thickness direction, the first sheet 32 may be constituted by one sheet of the stretchable sheet in which the colored elastic members 35 are provided, and the light transmittance of the first sheet 32 (non-skin side) may be greater than the light transmittance of the second sheet 33 (skin side). With this configuration, when viewed from the non-skin side of the waist portion 31 (41), the colored elastic member 35 is likely to be recognized, and this makes the stretchability of the waist portion 31 (41) of diaper 1 likely to be recognized, enabling to make the user likely to recall a good fit.

Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

REFERENCE SIGNS LIST 1 diaper (absorbent article, underpants-shaped disposable diaper),
10 absorbent main body,
10ea end portion, 10eb end portion, 10et upper end,
11 absorbent body, 11c absorbent core, 11ces end,
13 top sheet, 15 back sheet,
17 elastic string, 18 elastic string,
20 waist portion,
25 main-body joining portion,
31 front waist portion (stretchable sheet), 31e end portion,
32 first sheet, 33 second sheet,
35 elastic member, 351 elastic fiber,
37 damaged portion, 37v portion,
41 back waist portion (stretchable sheet), 41c buttocks cover,
41e end portion,
42 first sheet, 43 second sheet,
45 elastic member, 451 elastic fiber,
47 damaged portion,
48 leg elastic member,
50 welded portion,
50s welded portion pair, 50a upper welded portion, 50b lower welded portion,
51 first welded portion,
51s first welded portion pair, 51a upper welded portion, 51b lower welded portion,
51s1 outer first welded portion pair, 51s2 middle first welded portion pair, 51s3 inner first welded portion pair,
52 second welded portion,
52s second welded portion pair, 52a upper welded portion, 52b lower welded portion,
60 welded portion row,
70. side-joining-portion region,
71 side joining portion,
80 post-handling tape,
100 manufacturing line,
151 transport mechanism, 151R transport roller,
152 transport mechanism, 152R transport roller,
153 transport mechanism, 153R transport roller,
160 ultrasonic welding device,
161a anvil roll, 161at protrusion portion, 161h horn,
BH waist opening, LH leg opening,
CL1 center position,
CA central region, IA inner end region, OA outer end region,
SA absorbent-body side region, EA leg-circumferential region,
EB heat fused portion

What is claimed is:

1. A stretchable sheet comprising:
a first sheet;
a second sheet joined to the first sheet by welded portions; and
an elastic member that is disposed between the first sheet and the second sheet and stretches and contracts in a continuous direction in which the elastic member extends, wherein
the welded portions are disposed on both sides of the elastic member in an intersecting direction intersecting with the continuous direction,
welded portion pairs are disposed in which the elastic member is sandwiched and restrict a position of the elastic member in the intersecting direction with respect to the first sheet and the second sheet,
the elastic member has a damaged portion where a part of a surface of the elastic member is damaged,
the welded portion pairs include a first welded portion pair and a second welded portion pair that is disposed adjacent to the first welded portion pair in the continuous direction,
the damaged portion is disposed between the first welded portion pair and the second welded portion pair in the continuous direction.

2. The stretchable sheet according to claim 1, wherein when the elastic member is in a stretched state, an outer diameter of the elastic member in the damaged portion is larger than a gap of the welded portion pairs in the intersecting direction.

3. The stretchable sheet according to claim 1, wherein the elastic member is an aggregation of elastic fibers.

4. The stretchable sheet according to claim 3, wherein the elastic fibers are damaged in the damaged portion.

5. The stretchable sheet according to claim 4, wherein with respect to the continuous direction, in a portion of the elastic member where the damaged portion is formed, a number of damaged ones of the elastic fibers is smaller than a number of undamaged ones of the elastic fibers.

6. The stretchable sheet according to claim 3, wherein in the damaged portion, the elastic member has a portion where a damaged elastic fiber of the elastic fibers is peeled off from an undamaged elastic fiber of the elastic fibers.

7. The stretchable sheet according to claim 3, wherein the elastic member is twisted in the continuous direction.

8. The stretchable sheet according to claim 1, wherein
the welded portion pairs include a third welded portion pair and a fourth welded portion pair different from the first welded portion pair and the second welded portion pair and adjacent to each other in the continuous direction, and
the damaged portion is not disposed between the third welded portion pair and the fourth welded portion pair in the continuous direction.

9. The stretchable sheet according to claim 8, wherein a number of the welded portion pairs, disposed between a one-side end and an other-end end of the elastic member in the continuous direction, is greater than a number of damaged portions disposed between the one-side end and the other-end end of the elastic member in the continuous direction.

10. The stretchable sheet according to claim 1, wherein
the stretchable sheet has a thickness direction intersecting the continuous direction and the intersecting direction, and
the damaged portion does not have a portion that penetrates the first sheet and the second sheet in the thickness direction.

11. The stretchable sheet according to claim 1, wherein at least some elastic members are colored in a different color between the first sheet and the second sheet, and
the stretchable sheet has a portion satisfying either $X \leq 2$ or $S > N/2 - N/X$ where in the continuous direction,
S is a length of the welded portion pairs,
N is a distance between inner ends of two welded portion pairs that are in a stretched state and adjacent to each other, and
X is a value obtained by dividing a length of the stretchable sheet in the stretched state by a length of the stretchable sheet in a natural state.

12. The stretchable sheet according to claim 11, wherein the first welded portion pair:
is disposed on a one side in the continuous direction,
has one or more notched portions inbetween in the continuous direction, and
are divided by the one or more notched portions
the second welded portion pair is disposed on another side of and adjacent to the first welded portion pair, and
the stretchable sheet further satisfies $S2 > N/2 - N/X$ where
S2 is a value in the continuous direction obtained by subtracting a length of a located-farthest-on-one-side portion among divided portions of the first welded portion pair from the length of the first welded portion pair.

13. The stretchable sheet according to claim 11, wherein the stretchable sheet further satisfies $S > N/2 - N/2X$.

14. The stretchable sheet according to claim 11, wherein
the elastic members include uncolored ones, and
in the continuous direction, a total length of the welded portion pairs, disposed in a region where an elastic member that is colored is arranged, is longer than a total length of the welded portion pairs disposed in a region where an elastic member that is not colored is arranged.

15. The stretchable sheet according to claim 14, wherein a pitch of the elastic members in the intersecting direction in the region where an elastic member that is colored is arranged is smaller than a pitch of the elastic members in the intersecting direction in the region where an elastic member that is not colored is arranged.

16. The stretchable sheet according to claim 11, wherein either the first sheet or the second sheet is a nonwoven fabric sheet including titanium oxide, and
a content rate of the titanium oxide of the elastic member is less than 3.0%.

* * * * *